(12) United States Patent
Gerberding et al.

(10) Patent No.: US 12,005,205 B2
(45) Date of Patent: Jun. 11, 2024

(54) GUIDEWIRES FOR MEDICAL DEVICES

(71) Applicants: STRYKER CORPORATION, Kalamazoo, MI (US); STRYKER EUROPEAN OPERATIONS LIMITED, Carrigtwohill (IE)

(72) Inventors: Brent Gerberding, San Jose, CA (US); Hancun Chen, San Ramon, CA (US); Aleksandr Leynov, Walnut Creek, CA (US)

(73) Assignees: Stryker Corporation, Kalamazoo, MI (US); Stryker European Operations Limited, Carrigtwohill (IE)

( * ) Notice: Subject to any disclaimer, the term of this patent is extended or adjusted under 35 U.S.C. 154(b) by 147 days.

(21) Appl. No.: 16/716,280

(22) Filed: Dec. 16, 2019

(65) Prior Publication Data
US 2021/0178127 A1    Jun. 17, 2021

(51) Int. Cl.
*A61M 25/09* (2006.01)
*A61M 25/00* (2006.01)

(52) U.S. Cl.
CPC .......... *A61M 25/09* (2013.01); *A61M 25/007* (2013.01); *A61M 2025/09091* (2013.01); *A61M 2025/09166* (2013.01); *A61M 2025/09175* (2013.01)

(58) Field of Classification Search
CPC ........ A61M 25/09; A61M 2025/09091; A61M 2025/09166; A61M 2025/09175; A61M 2025/09075; A61M 2025/09083; A61M 2025/0915
See application file for complete search history.

(56) References Cited

U.S. PATENT DOCUMENTS

| | | | | |
|---|---|---|---|---|
| 5,067,489 A | * | 11/1991 | Lind | A61M 25/09033 600/585 |
| 5,465,732 A | * | 11/1995 | Abele | A61M 25/09 600/585 |
| 5,957,865 A | * | 9/1999 | Backman | A61M 25/09 600/585 |
| 6,329,069 B1 | * | 12/2001 | Azizi | B21C 37/042 428/685 |
| 8,128,580 B2 | | 3/2012 | Fujimagari et al. | |

(Continued)

FOREIGN PATENT DOCUMENTS

| | | |
|---|---|---|
| CN | 103301553 | 9/2013 |
| CN | 106231999 | 12/2016 |

(Continued)

OTHER PUBLICATIONS

PCT Invitation to Pay Additional Fees for International Appln. No. PCT/US2020/063927, Applicant Stryker Corporation, dated May 10, 2021 (14 pages).

(Continued)

*Primary Examiner* — Sean P Dougherty
(74) *Attorney, Agent, or Firm* — Vista IP Law Group, LLP

(57) ABSTRACT

A guidewire includes: a shaft having a proximal end, a distal end, and a body extending from the proximal end to the distal end; a blunt tip; and a sleeve; wherein the body of the shaft comprises at least a segment that is surrounded by the sleeve, the segment coupled to the blunt tip; and wherein the segment of the body of the shaft comprises a flat portion having one or more openings extending through a thickness of the flat portion.

4 Claims, 10 Drawing Sheets

(56) References Cited

U.S. PATENT DOCUMENTS

| | | | |
|---|---|---|---|
| 8,939,916 B2* | 1/2015 | Jacobsen | A61M 25/09016 600/585 |
| 10,258,240 B1* | 4/2019 | Eberle | A61B 5/0084 |
| 2002/0058888 A1* | 5/2002 | Biagtan | A61M 25/09 600/585 |
| 2003/0023190 A1* | 1/2003 | Cox | A61M 25/0045 600/585 |
| 2004/0167437 A1 | 8/2004 | Sharrow et al. | |
| 2004/0167443 A1* | 8/2004 | Shireman | A61M 25/09 600/585 |
| 2004/0210163 A1* | 10/2004 | Osawa | A61M 25/09 600/585 |
| 2005/0148866 A1* | 7/2005 | Gunderson | A61M 25/0108 600/431 |
| 2007/0185414 A1* | 8/2007 | Urbanski | A61M 25/09 600/585 |
| 2007/0185415 A1* | 8/2007 | Ressemann | A61M 25/09025 600/585 |
| 2007/0244413 A1* | 10/2007 | Biggins | A61M 25/09 600/585 |
| 2007/0249964 A1* | 10/2007 | Richardson | A61M 25/09 600/585 |
| 2008/0004546 A1* | 1/2008 | Kato | A61M 25/09 600/585 |
| 2008/0119762 A1* | 5/2008 | Tateishi | A61M 25/09 72/364 |
| 2008/0140010 A1* | 6/2008 | Kennedy | A61M 25/0169 604/164.05 |
| 2008/0146967 A1* | 6/2008 | Richardson | A61M 25/09 600/585 |
| 2009/0036768 A1* | 2/2009 | Seehusen | A61L 29/18 604/529 |
| 2009/0076416 A1 | 3/2009 | Treacy et al. | |
| 2009/0177119 A1* | 7/2009 | Heidner | A61M 25/09 600/585 |
| 2009/0254000 A1* | 10/2009 | Layman | A61M 25/01 600/585 |
| 2010/0191150 A1* | 7/2010 | Palme, Jr. | A61M 25/09033 600/585 |
| 2011/0118628 A1* | 5/2011 | Zhou | A61M 25/09 600/585 |
| 2011/0208092 A1* | 8/2011 | Nishigishi | A61M 25/09 600/585 |
| 2012/0203207 A1* | 8/2012 | Northrop | A61M 25/09033 604/528 |
| 2012/0245488 A1* | 9/2012 | Matsumoto | A61M 25/09 600/585 |
| 2012/0265079 A1* | 10/2012 | Hilmersson | A61B 5/6851 600/549 |
| 2013/0046202 A1* | 2/2013 | Tsunezumi | A61M 25/09 600/585 |
| 2013/0197310 A1* | 8/2013 | Hino | A61M 25/09041 600/153 |
| 2013/0237963 A1* | 9/2013 | Stiger | C23F 4/00 604/529 |
| 2014/0094741 A1* | 4/2014 | Bellisario | A61M 1/3661 604/39 |
| 2016/0331943 A1* | 11/2016 | Lupton | A61B 17/22 |
| 2017/0106172 A1* | 4/2017 | Ootani | A61M 25/09 |
| 2017/0120018 A1* | 5/2017 | Ootani | A61M 25/09 |
| 2017/0239453 A1* | 8/2017 | Kawakita | A61M 25/09 |
| 2018/0015255 A1* | 1/2018 | Bonnette | A61M 5/142 |
| 2018/0093078 A1* | 4/2018 | Patil | A61B 5/6851 |
| 2018/0296805 A1 | 10/2018 | Eskuri | |
| 2019/0030300 A1* | 1/2019 | Dant | A61M 25/09 |
| 2019/0184143 A1* | 6/2019 | Onushko | A61B 17/22 |
| 2019/0298989 A1 | 10/2019 | Gardeski et al. | |
| 2020/0222672 A1* | 7/2020 | Davis | A61M 25/09 |
| 2020/0238054 A1* | 7/2020 | Tsuge | A61M 25/09 |
| 2021/0000421 A1* | 1/2021 | Sawai | A61B 5/6876 |
| 2021/0060299 A1* | 3/2021 | Amin | A61M 25/0102 |
| 2021/0060310 A1* | 3/2021 | Kim | A61M 25/09041 |

FOREIGN PATENT DOCUMENTS

| | | |
|---|---|---|
| EP | 2647404 | 10/2013 |
| JP | 2017-164200 | 9/2017 |
| JP | 2017164200 | 9/2017 |
| JP | 2017164200 A * | 9/2017 |

OTHER PUBLICATIONS

PCT International Search Report and Written Opinion for International Appln. No. PCT/US2020/063927, Applicant Stryker Corporation, dated Jul. 6, 2021 (16 pages).

Extended European Search Report for EP Patent Appln. No. 23169264.1 dated Sep. 15, 2023.

Foreign OA for CN Patent Appln. No. 202080088011.3 dated Nov. 23, 2023 (with English summary of examiner's opinion).

Foreign OA for CN Patent Appln. No. 202080088011.3 dated Mar. 12, 2024 (with English summary of examiner's opinion).

* cited by examiner

GUIDEWIRES FOR MEDICAL DEVICES

FIELD

The field of the application relates to medical devices, and more specifically, to guidewires for medical devices, and medical devices having such guidewires.

BACKGROUND

Guidewires have been used in the medical field to access passages inside patients. In some cases, it may be desirable for a guidewire to have good torqueability, which allows a torque motion applied about a longitudinal axis of the guidewire at a proximal end of the guidewire to cause a corresponding twisting motion at a distal end of the guidewire.

Also, it may be desirable for a distal segment of a guidewire to retain a certain bent shape during use. This allows the distal segment of the guidewire to access certain passage with specific geometry inside the patient. If the distal segment of the guidewire cannot retain its bent shape during use, then it may not be able to access a target passage.

In addition, it may be desirable for a guidewire to have a soft distal segment. This prevents the guidewire from causing injury to the patient, and also allows the guidewire to elastically flex or bend as it is advanced inside the patient through passages of different shapes.

However, it is difficult for a guidewire to achieve all of the above desirable features. A guidewire may have a soft distal segment, but such guidewire may have poor shape retention ability at the distal segment and poor torqueability. On the other hand, a guidewire may have great shape retention ability at the distal segment and good torqueability. However, such guidewire may have a stiff distal segment. The above desirable features are difficult to accomplish together because a soft distal segment of a guidewire usually cannot achieve good torqueability due to the softness of the material that is used to make the distal segment. Also, the material that is used to make the soft distal guidewire segment may not allow the distal guidewire segment to maintain its shape during use.

New guidewires for medical devices would be desirable.

SUMMARY

A guidewire includes: a shaft having a proximal end, a distal end, and a body extending from the proximal end to the distal end; a blunt tip; and a sleeve; wherein the body of the shaft comprises at least a segment that is surrounded by the sleeve, the segment coupled to the blunt tip; and wherein the segment of the body of the shaft comprises a flat portion having one or more openings extending through a thickness of the flat portion.

Optionally, the one or more openings comprise only one elongated slot extending through the thickness of the flat portion.

Optionally, the flat portion has a long side that is parallel to a longitudinal axis of the guidewire, and wherein the slot has a long side that is parallel to the long side of the flat portion.

Optionally, the one or more openings comprise a series of openings arrange along a longitudinal axis of the flat portion.

Optionally, each of the openings in the series is a rectangular slot extending through the thickness of the flat portion.

Optionally, each of the openings in the series is a circular slot extending through the thickness of the flat portion.

Optionally, the one or more openings comprise rows of openings arranged in a staggered configuration.

Optionally, the guidewire further includes a radiopaque marker extending through one of the one or more openings.

Optionally, the radiopaque marker has a first portion abutting a first side of the flat portion, a second portion within the one of the one or more openings, and a third portion abutting a second side of the flat portion, the second side being opposite from the first side of the flat portion.

Optionally, the first portion of the radiopaque marker has a first cross sectional dimension, the second portion of the radiopaque marker has a second cross sectional dimension, and the third portion of the radiopaque marker has a third cross sectional dimension; wherein the first cross sectional dimension is larger than the second cross sectional dimension; and wherein the third cross sectional dimension is larger than the second cross sectional dimension.

Optionally, the flat portion comprises a stamped core wire.

Optionally, the guidewire further includes a coil disposed between the flat portion and the sleeve.

Optionally, the coil is made from a radiopaque material.

Optionally, the coil is made from Platinum Tungsten.

Optionally, the sleeve is made from Nitinol.

Optionally, the sleeve comprises a plurality of slots.

Optionally, the body of the shaft comprises a tapering portion that is proximal the flat portion.

Optionally, the body of the shaft comprises a cylinder portion that is proximal the tapering portion.

Optionally, the flat portion is bendable to form a bent shape and is configured to retain the bent shape after the flat portion is bent.

Optionally, the segment also comprises an additional flat portion distal to the flat portion.

Optionally, the segment also comprises a connecting portion connecting the flat portion and the additional flat portion, wherein the connecting portion, the flat portion, and the additional flat portion have an unity configuration.

A medical device includes a catheter, and the guidewire, wherein the catheter includes a lumen for accommodating the guidewire.

A guidewire includes: a shaft having a proximal end, a distal end, and a body extending from the proximal end to the distal end; a blunt tip; and a sleeve; wherein the body of the shaft comprises at least a segment that is surrounded by the sleeve, the segment coupled to the blunt tip; and wherein the segment of the body of the shaft comprises a flat portion with a first major surface and a second major surface opposite from the first major surface, and wherein the flat portion comprises one or more radiopaque markers secured on the first major surface.

Optionally, the one or more radiopaque markers comprise a first planar marker having a width that is the same as a width of the flat portion.

Optionally, the guidewire further includes a second planar marker secured on the second major surface of the flat portion.

Optionally, the one or more radiopaque markers comprise first multiple radiopaque markers spaced apart from each other.

Optionally, the first multiple radiopaque markers are aligned in a row along a longitudinal axis of the flat portion.

Optionally, the guidewire further includes second multiple radiopaque markers spaced apart from each other and secured on the second major surface of the flat portion.

Optionally, the flat portion also comprises one or more radiopaque markers secured on the second major surface.

A guidewire includes: a shaft having a proximal end, a distal end, and a body extending from the proximal end to the distal end; a blunt tip; and a sleeve; wherein the body of the shaft comprises at least a segment that is surrounded by the sleeve, the segment coupled to the blunt tip; and wherein the segment of the body of the shaft comprises a flat portion with an exterior surface, and wherein the flat portion comprises a plurality of grooves at the exterior surface.

A guidewire includes: a shaft having a proximal end, a distal end, and a body extending from the proximal end to the distal end; a blunt tip; and a sleeve; wherein the body of the shaft comprises at least a segment that is surrounded by the sleeve, the segment coupled to the blunt tip; and wherein the guidewire further comprises a radiopaque coil surrounding at least a part of the segment, the part of the segment having opposite sides with indentations along each of the opposite sides for allowing the radiopaque coil to be screwed over the part of the segment.

Optionally, the part of the segment comprises a flat portion.

Optionally, the segment comprises a flat portion, and the part of the segment is proximal to the flat portion.

Other and further aspects and features will be evident from reading the following detailed description.

DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

DETAILED DESCRIPTION

Figure 1A:
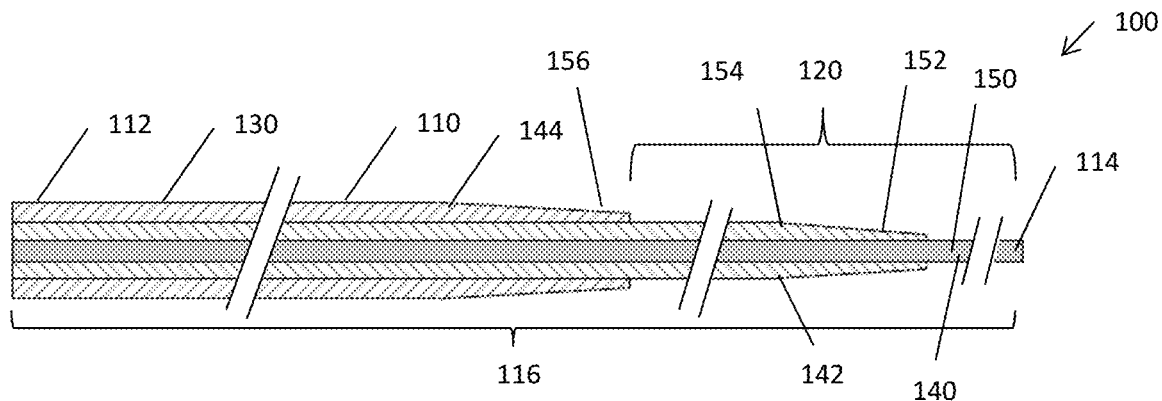
FIG. 1A illustrates a guidewire.

Various embodiments are described hereinafter with reference to the figures. It should be noted that the figures are not drawn to scale and that elements of similar structures or functions are represented by the same reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1A illustrates a guidewire 100 in accordance with some embodiments. The guidewire 100 includes a shaft 110 having a proximal end 112, a distal end 114, and a body 116 extending from the proximal end 112 to the distal end 114. The body 116 of the shaft 110 comprises a distal segment 120 having a plurality of different cross sections along a length of the distal segment 120. At least an outer part 130 of the body 116 that is proximal to the distal segment 120 is made of a material having a shear modulus of at least 13000 ksi. By means of non-limiting examples, the material of the outer part 130 of the body is Molybdenum Rhenium alloy or Tungsten Rhenium alloy.

In the illustrated embodiments, the shaft 110 includes a first layer 140, a second layer 142, and a third layer 144. The third layer 144 is outside the second layer 142, and the second layer 142 is outside the first layer 140. As shown in the figure, the third layer 144 comprises the outer part 130 of the body 116 that is proximal to the distal segment 120. In some embodiments, the third layer 144 of the shaft 110 may be made from Molybdenum Rhenium alloy or Tungsten Rhenium alloy. Also, in some embodiments, the first layer 140 may be made of Molybdenum Rhenium alloy, Tungsten Rhenium alloy, stainless steel, Nitinol, NeoNickel alloy (e.g., MP35N alloy), or Cobalt-Chromium alloy. The second layer 142 may be made from Nitinol, or any of the other materials.

In the illustrated embodiments, a part 150 of the first layer 140 is distal to a distal end 152 of the second layer 142, and a part 154 of the second layer 142 is distal to a distal end 156 of the third layer 144, thereby allowing the part 150 of the first layer 140 and the part 154 of the second layer 142 to form at least a portion of the distal segment 120 of the body 116 of the shaft 110. Such configuration is advantageous because it provides the distal segment 120 having a cross sectional dimension that is smaller compared to that of a remaining part of the body 116 (that is proximal to the distal segment 120). As a result, the distal segment 120 is softer compared to the remaining part of the body 116, and may flex or bend more easily.

In some embodiments, the part 150 of the first layer 140 may be compressed to form an elongated cross sectional shape for the part 150 of the first layer 140. For example, in one implementation, the first layer 140 may have a circular cross sectional shape, and the part 150 of the first layer 140 may be compressed into a planar structure having an elongated cross sectional shape, or any of other non-circular cross sections. This feature is advantageous because it provides a bias in the direction of bending for the part 150 of the first layer 140. The compressing of the part 150 of the first layer 140 may be achieved by stamping the part 150 of the first layer 140 in some embodiments.

In one specific implementation, both the first and third layers 140, 144 are made from Molybdenum Rhenium alloy, and the second layer 142 is made from Nitinol that is sandwiched between the two Molybdenum Rhenium alloy layers 140, 144. In another specific implementation, the first layer 140 is made from stainless steel or Cobalt-Chromium alloy (e.g., MP35N alloy), the second layer 142 is made from Nitinol, and the third layer is made from Molybdenum Rhenium alloy. In either implementation, the Nitinol layer 142 provides kink resistance and a softer distal segment 120. The first layer 140 is shapeable during use, and provides desirable shape retention capability. Also, because of its relatively high shear modulus, the outer Molybdenum Rhenium alloy layer 144 provides a desirable torqueability. Furthermore, because of the axial stiffness of the outer Molybdenum Rhenium alloy layer 144, the guidewire 100 also has a desirable pushability.

Figure 1B:
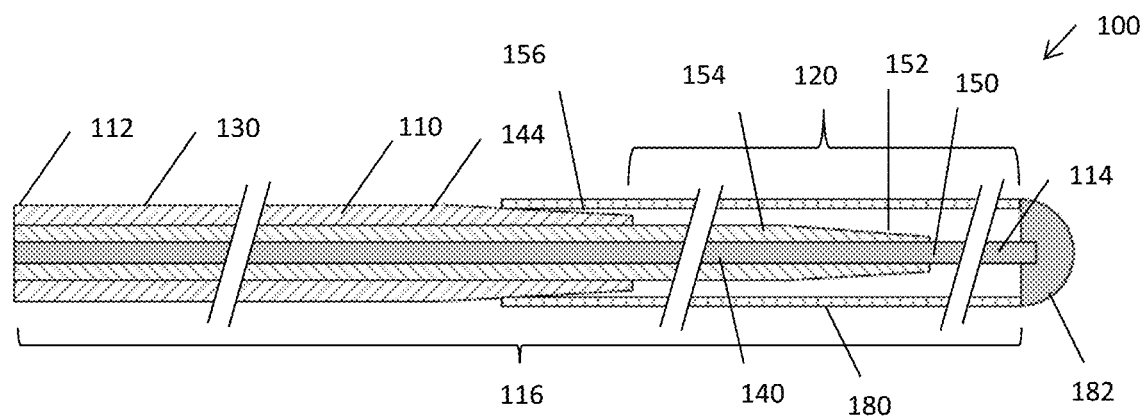
FIG. 1B illustrates the guidewire of FIG. 1A, further having a sleeve and a tip.

As shown in FIG. 1B, in some embodiments, the guidewire 100 may also include a sleeve 180 disposed around at least a part of the distal segment 120 (e.g., the distal end 114) of the shaft 110. As shown in the figure, the sleeve 180 has a blunt tip 182. The distal end 114 of the shaft 110 is coupled to the blunt tip 182. The sleeve 180 may be any tubular member, and may be made from any materials, such as metal, polymer, etc. In some embodiments, the sleeve 180 may be made from Nitinol. The sleeve 180 may have a plurality of slots and/or openings to increase a flexibility of the sleeve 180. By means of non-limiting examples, the sleeve 180 may be implemented using slotted hypotube, coiled sleeve, tungsten-loaded polymer sleeve, or a combination of the foregoing.

Figure 1C:
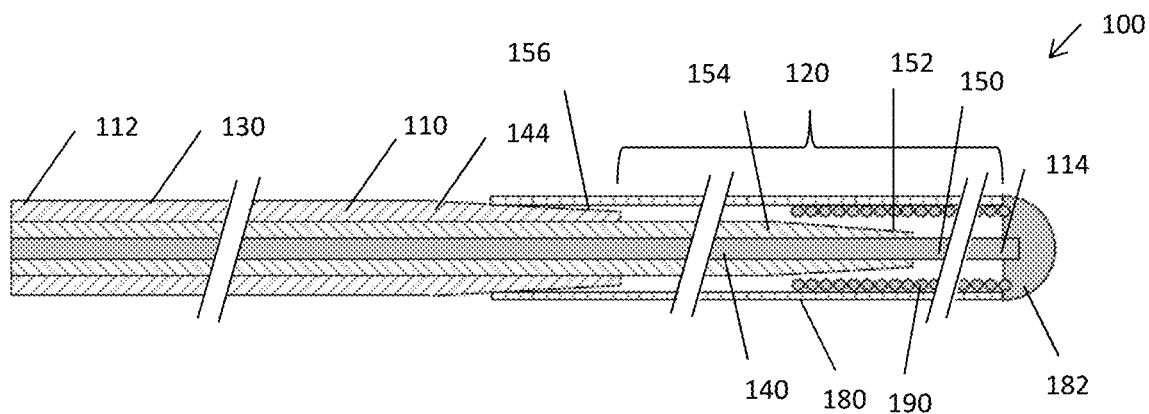
FIG. 1C illustrates the guidewire of FIG. 1B, further having a coil.
Figure 1D:
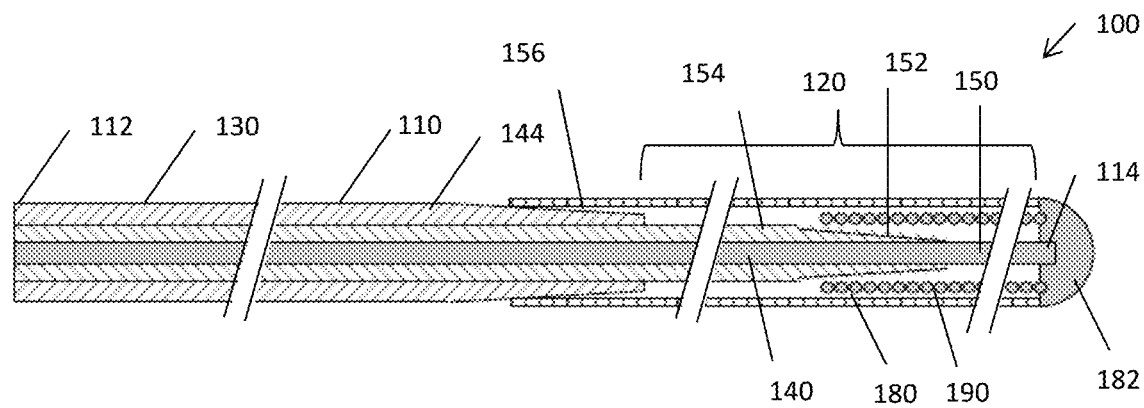
FIG. 1D illustrates the guidewire of FIG. 1B, further having a coil that is spaced away from a wall of a sleeve.
Figure 1E:
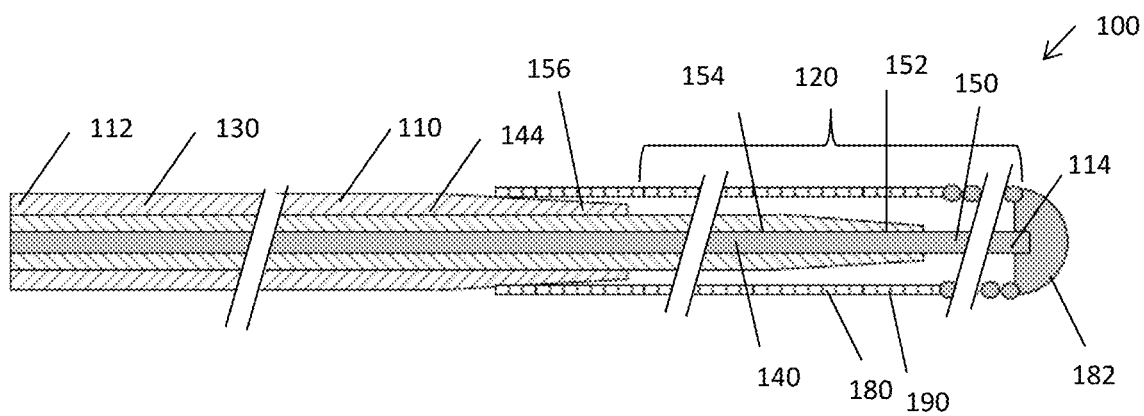
FIG. 1E illustrates the guidewire of FIG. 1A, further having a sleeve and a tip.

Referring to FIG. 1C, in some embodiments, the guidewire 100 may also include a marker coil 190 disposed inside the sleeve 180. As shown in the figure, one end of the marker coil 190 is secured to the tip 182, while a body of the marker coil 190 is secured to or is abut against a wall of the sleeve 180. In other embodiments, the coil 190 may be coupled to only the tip 182, and not to the wall of the sleeve 180 (FIG. 1D). In other embodiments, the proximal end of the marker coil 190 may be secured to the second layer 154 (e.g., to the distal end 152 of the second layer 154), such as by an adhesive, welding, mechanical connector, fusion, etc. In further embodiments, at least a part of the sleeve 180 may be formed by the marker coil 190 (FIG. 1E). As shown in the figure, the marker coil 190 has a cross sectional dimension that corresponds with (e.g., is the same as) a cross sectional dimension of the sleeve 180. In some cases, an entirety of the length of the sleeve 180 may be made from a coil, such as a marker coil.

In the illustrated embodiments of FIGS. 1A-1E, the distal part 150 of the segment 120 is malleable. Thus, the distal part 150 of the segment 120 is bendable to form a bent shape. The distal part 150 is made from a material that allows it to retain the bent shape after the distal part 150 of the segment 120 is bent. In other embodiments, the distal part 150 (or the first layer 140 comprising the distal part 150) may be made from a material that does not have sufficient shape retention capability. In such cases, the guidewire 100 may further include a malleable structure attached to the blunt tip 182. The malleable structure may be inside the sleeve 180. During use, the malleable structure is bendable to form a bent shape and is configured to retain the bent shape after the malleable structure is bent. In some embodiments, the malleable structure may be made from Molybdenum Rhenium alloy or Tungsten Rhenium alloy.

The guidewire 100 is advantageous because it provides a desirable torqueability, a desirable pushability, and a desirable shape retention ability, while achieving a desirable softness at the distal segment 120. In particular, the outermost layer 144 provides a desirable torqueability due to it being made from a material having a sufficiently high (e.g., of at least 13000 ksi) shear modulus. Also, the distal segment 120 has a desirable bending stiffness, and the distal part 150 also has a desirable bending stiffness and shape retention capability. Accordingly, the guidewire 100 has optimal combination of soft distal segment, shapeability, and torqueability.

Figure 1F:
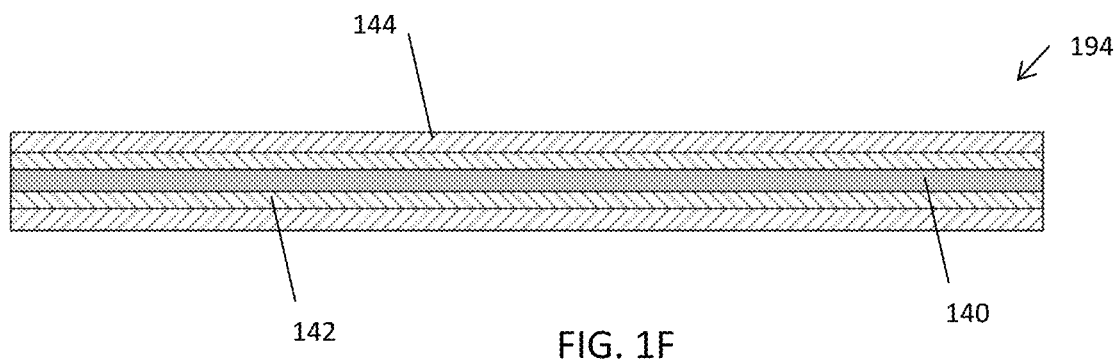
FIG. 1F illustrates a member for making a guidewire.

FIG. 1F illustrates a member 194 for making the guidewire 100. The member 194 includes the first layer 140, the second layer 142, and the third layer 144. In some embodiments, a part of the third layer 144 may be removed to expose the part 154 of the second layer 142. Also, a part of the second layer 142 may be removed to expose the part 150 of the first layer 140. The above actions will result in the shaft 110 having multiple different cross sectional shapes along its length, like that shown in FIGS. 1A-1E. In some embodiments, the removing of the part of the third layer 144, and the part of the second layer 142, may be accomplished by grinding, cutting, sanding, or any combination of the foregoing.

In the above embodiments, the shaft 110 of the guidewire 100 has three layers 140, 142, 144. In other embodiments, the shaft 110 of the guidewire 100 may have more than three layers, or fewer than three layers (e.g., two layers).

Figure 2A:
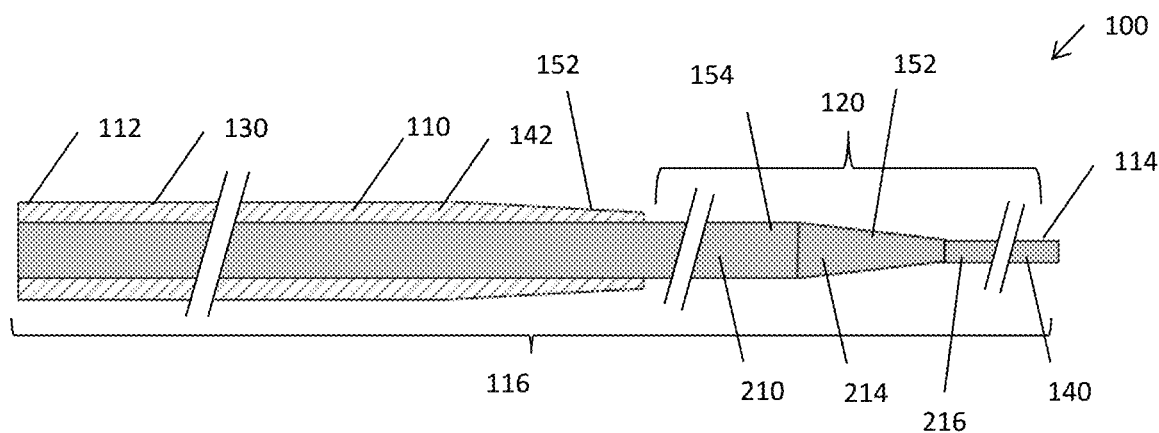
FIG. 2A illustrates a guidewire.

FIG. 2A illustrates a guidewire 100 in accordance with some embodiments. Unlike the guidewire of FIG. 1A, the guidewire 100 of FIG. 2A has only two layers 140, 142. Refer to FIG. 2A, the guidewire 100 includes a shaft 110 having a proximal end 112, a distal end 114, and a body 116 extending from the proximal end 112 to the distal end 114. The body 116 of the shaft 110 comprises a distal segment 120 having a plurality of different cross sections along a length of the distal segment 120. At least an outer part 130 of the body 116 that is proximal to the distal segment 120 is made of a material having a shear modulus of at least 13000 ksi. By means of non-limiting examples, the material of the outer part 130 of the body is Molybdenum Rhenium alloy or Tungsten Rhenium alloy.

In the illustrated embodiments, the shaft 110 includes a first layer 140, and a second layer 142. The second layer 142 is outside the first layer 140. As shown in the figure, the second layer 142 comprises the outer part 130 of the body 116 that is proximal to the distal segment 120. In some embodiments, the second layer 142 of the shaft 110 may be made from Molybdenum Rhenium alloy or Tungsten Rhenium alloy. Also, in some embodiments, the first layer 140 may be made of a material having a shear modulus that is less than the shear modulus of the second layer 142. By means of non-limiting examples, the first layer 140 may be made from stainless steel, Nitinol, Cobalt-Chromium alloy (e.g., MP35N alloy), etc.

In the illustrated embodiments, the segment 120 of the shaft 110 is made from the first layer 140. The segment 120 is distal to a distal end 152 of the second layer 142. The segment 120 of the first layer 140 has a first part 210, a second part 214, and a third part 216. The third part 216 has a cross sectional dimension that is smaller compared to a cross sectional dimension of the first part 210, and the smaller cross sectional dimension of the third part 216 transitions into the larger cross section dimension of the first part 210 via the second (intermediate) part 214. Such configuration is advantageous because it provides progressively softer sections in the proximal-to-distal direction. As a result, the distal segment 120 is softer compared to the remaining part of the body 116, with the distal part 216 providing the softest section, and may flex or bend more easily. In other embodiments, the segment 120 may comprise more parts or fewer parts than those described above.

In some embodiments, the third part 216 of the segment 120 may be compressed to form an elongated cross sectional shape for the part 216 of the segment 120. For example, in one implementation, the first layer 140 may have a circular cross sectional shape, and the part 216 of the first layer 140 may be compressed into a planar structure having an elongated cross sectional shape, or any of other non-circular shapes. This feature is advantageous because it provides a bias in the direction of bending for the part 216 of the first layer 140. The compressing of the part 216 of the first layer 140 may be achieved by stamping the part 216 of the first layer 140 in some embodiments.

In one specific implementation, the second layer 142 is made from Molybdenum Rhenium alloy, and the first layer 140 is made from Nitinol. The inner Nitinol layer 140 provides kink resistance and a soft distal end for the guidewire 100, while the outer layer 142 provides a desired pushability and a desired torqueability. In another specific implementation, the second layer 142 is made from Molybdenum Rhenium alloy, and the first layer 140 is made from stainless steel, or Cobalt-Chromium alloy (e.g., MP35N alloy). The first layer 140 provides kink resistance and a softer distal segment 120. The first layer 140 may be shapeable during use, and provides desirable shape retention capability (e.g., with or without the aid of a malleable structure). Also, because of its relatively high shear modulus, the outer Molybdenum Rhenium alloy layer 142 provides a desirable torqueability. Furthermore, because of the axial stiffness of the outer Molybdenum Rhenium alloy layer 142, the guidewire 100 also has a desirable pushability.

Figure 2B:
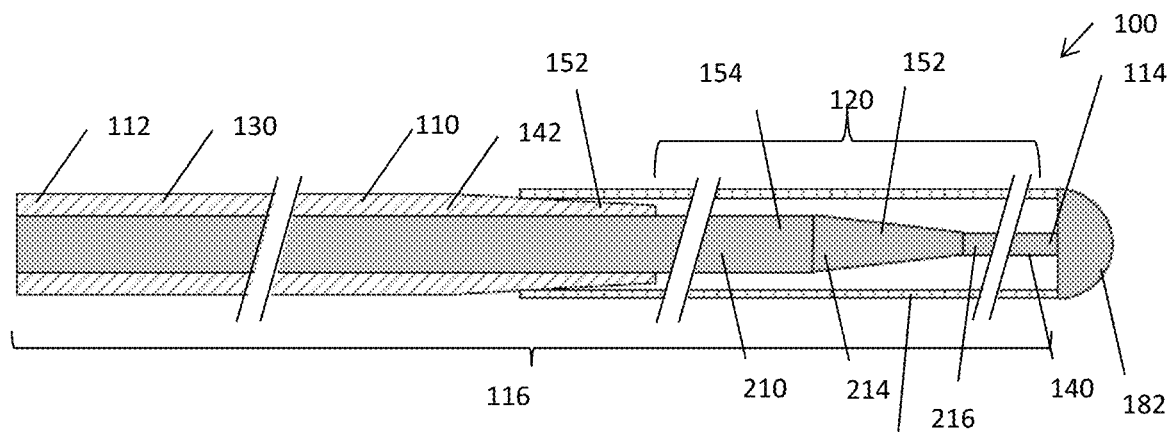
FIG. 2B illustrates the guidewire of FIG. 2A, further having a sleeve and a tip.

As shown in FIG. 2B, in some embodiments, the guidewire 100 may also include a sleeve 180 disposed around at least a part of the distal segment 120 (e.g., the distal end 114) of the shaft 110. As shown in the figure, the sleeve 180 has a blunt tip 182. The distal end 114 of the shaft 110 is coupled to the blunt tip 182. The sleeve 180 may be any tubular member, and may be made from any materials, such as metal, polymer, etc. In some embodiments, the sleeve 180 may be made from Nitinol. The sleeve 180 may have a plurality of slots and/or openings to increase a flexibility of the sleeve 180. By means of non-limiting examples, the sleeve 180 may be implemented using slotted hypotube, coiled sleeve, tungsten-loaded polymer sleeve, or a combination of the foregoing.

Figure 2C:
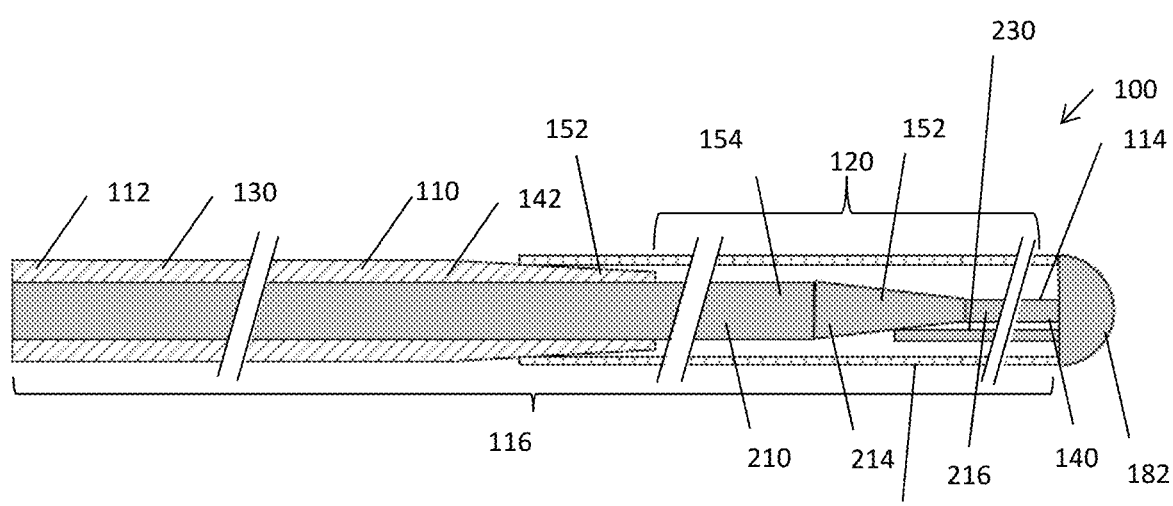
FIG. 2C illustrates the guidewire of FIG. 2B, further having a malleable structure.

In the illustrated embodiments of FIGS. 2A-2B, the distal part 216 of the segment 120 is malleable. Thus, the distal part 216 of the segment 120 is bendable to form a bent shape. The distal part 216 is made from a material that allows it to retain the bent shape after the distal part 216 of the segment 120 is bent. In other embodiments, as shown in FIG. 2C, the distal part 216 (or the first layer 140 comprising the distal part 216) may be made from a material that does not have sufficient shape retention capability. In such cases, the guidewire 100 may further include a malleable structure 230 attached to the blunt tip 182. The malleable structure 230 may be inside the sleeve 180. During use, the malleable structure 230 is bendable to form a bent shape and is configured to retain the bent shape after the malleable structure 230 is bent. In some embodiments, the malleable structure 230 may be made from Molybdenum Rhenium alloy or Tungsten Rhenium alloy, in order to provide a desirable shape retention ability for the guidewire 100.

Figure 2D:
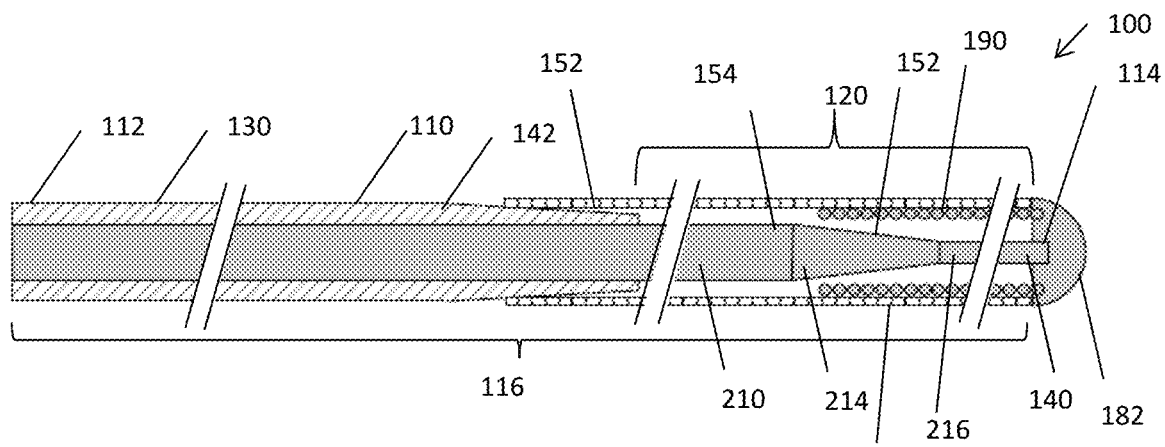
FIG. 2D illustrates the guidewire of FIG. 2B, further having a coil.

Referring to FIG. 2D, in some embodiments, the guidewire 100 may also include a marker coil 190 disposed inside the sleeve 180. As shown in the figure, one end of the marker coil 190 is secured to the tip 182, while a body of the marker coil 190 is secured to or is abut against a wall of the sleeve 180. In other embodiments, the coil 190 may be coupled to only the tip 182, and not to the wall of the sleeve 180. In other embodiments, the proximal end of the marker coil 190 may be secured to the distal segment 120 (e.g., to any location that is proximal to the part 216, such as to the part 214, the part 210, etc.). The securing may be accomplished using an adhesive, welding, mechanical connector, fusion, etc. In further embodiments, at least a part of the sleeve 180 may be formed by the marker coil 190. In such cases, the marker coil 190 has a cross sectional dimension that corresponds with (e.g., is the same as) a cross sectional dimension of the sleeve 180. In some cases, an entirety of the length of the sleeve 180 may be made from a coil, such as a marker coil.

Figure 2E:
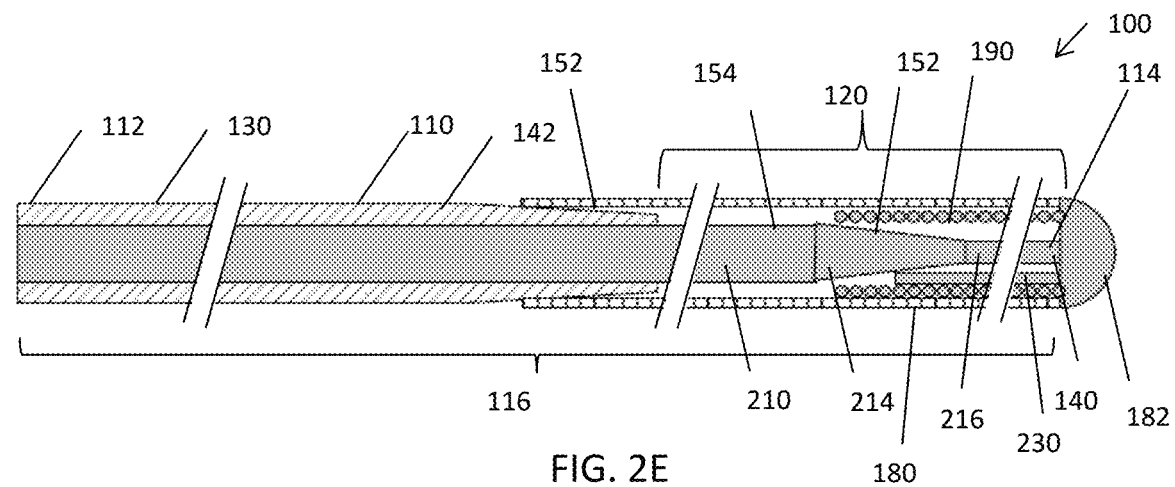
FIG. 2E illustrates the guidewire of FIG. 2D, further having a malleable structure and a coil.

In some embodiments, the guidewire 100 may include both the malleable structure 230 and the marker coil 190 (FIG. 2E).

Figure 2F:
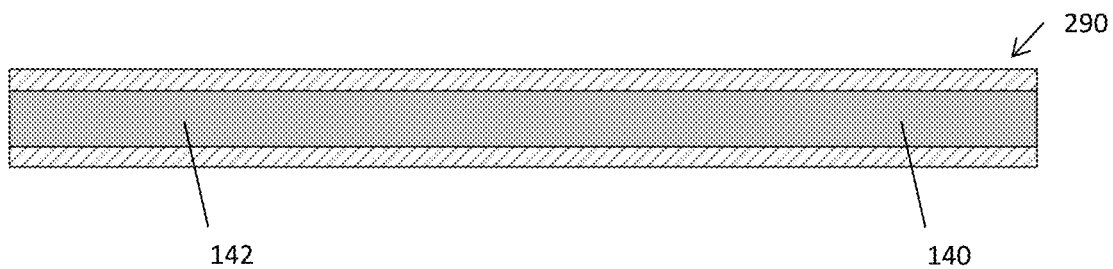
FIG. 2F illustrates a member for making a guidewire.

FIG. 2F illustrates a member 290 for making a guidewire. The member 290 includes the first layer 140, and the second layer 142. In some embodiments, a part of the second layer 142 may be removed to expose the first layer 140. Also, parts of the exposed first layer 140 may be removed, with more material being removed distally than proximally. The above actions will result in the shaft 110 having multiple different cross sectional shapes along its length, like that shown in FIGS. 2A-2E. In some embodiments, the removing of the part of the second layer 142, and the part of the exposed first layer 140, may be accomplished by grinding, cutting, sanding, or any combination of the foregoing.

Figure 3A:
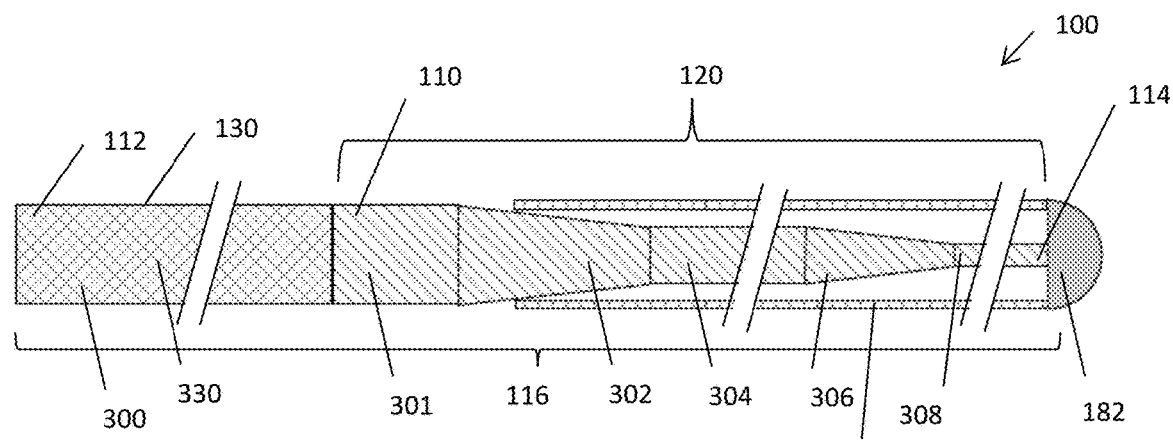
FIG. 3A illustrates a guidewire.

In further embodiments, the shaft 110 of the guidewire 100 may have a single layer. FIG. 3A illustrates a guidewire 100 in accordance with some embodiments. Unlike the guidewire of FIG. 1A and FIG. 1B, the guidewire 100 of FIG. 3A has only one layer in each of a distal segment and a proximal segment of the shaft 110. Refer to FIG. 3A, the guidewire 100 includes a shaft 110 having a proximal end 112, a distal end 114, and a body 116 extending from the proximal end 112 to the distal end 114. The body 116 of the shaft 110 comprises a distal segment 120 having a plurality of different cross sections along a length of the distal segment 120. At least an outer part 130 of the body 106 that is proximal to the distal segment 120 is made of a material having a shear modulus of at least 13000 ksi. By means of non-limiting examples, the material of the outer part 130 of the body is Molybdenum Rhenium alloy or Tungsten Rhenium alloy.

In the illustrated embodiments, the shaft 110 includes a proximal segment 300 made of a first material, and the distal segment 120 is made from a second material that is different from the first material. In some embodiments, the proximal segment 300 may be made from Molybdenum Rhenium alloy or Tungsten Rhenium alloy. Also, in some embodiments, the distal segment 120 may be made from Nitinol, stainless steel, or Cobalt-Chromium alloy (e.g., MP35N alloy).

As shown in the figure, the distal segment 120 has a single layer, and includes a first part 301, a second part 302, a third part 304, a fourth part 306, and a fifth part 308. The fifth part 308 has a cross sectional dimension that is smaller compared to a cross sectional dimension of the third part 304, and the smaller cross sectional dimension of the fifth part 308 transitions into the larger cross section dimension of the third part 304 via the fourth (intermediate) part 306. Similarly, the third part 304 has a cross sectional dimension that is smaller compared to a cross sectional dimension of the first part 301, and the smaller cross sectional dimension of the third part 304 transitions into the larger cross section dimension of the first part 301 via the second (intermediate) part 302. Such configuration is advantageous because it provides progressively softer sections in the proximal-to-distal direction. As a result, the distal segment 120 is softer compared to the remaining part of the body 116, with the distal part 308 providing the softest section, and may flex or bend more easily. In other embodiments, the distal segment 120 may comprise more parts or fewer parts than those described above.

The proximal segment 300 also has a single layer. The proximal segment 300 may be attached to the distal segment 120 via an adhesive, weld, mechanical connector, or fusion.

As shown in the figure, an inner part 330 of the body 116 that is proximal to the segment 120 and the outer part 300 of the body 116 that is proximal to the segment 120 are made from the same material (as shown by the shaded cross section). In one implementation, the outer part 300 and the inner part 330 of the body 116 are made from a same piece of raw material (e.g., Molybdenum Rhenium alloy, Tungsten Rhenium alloy, etc.), so that they have an unity configuration.

In some embodiments, the part 308 of the segment 120 may be compressed to form an elongated cross sectional shape for the part 308. For example, in one implementation, the part 308 may have a circular cross sectional shape, and the part 308 of the segment 120 may be compressed into a planar structure having an elongated cross sectional shape, or any of other non-circular cross sectional shapes. This feature is advantageous because it provides a bias in the direction of bending for the part 308. The compressing of the part 308 may be achieved by stamping the part 308 in some embodiments.

In the illustrated embodiments, the guidewire 100 also includes a sleeve 180 disposed around the distal end 114 of the shaft 110. As shown in the figure, the sleeve 180 has a blunt tip 182. The distal end 114 of the shaft 110 is coupled to the blunt tip 182. The sleeve 180 may be any tubular member, and may be made from any materials, such as metal, polymer, etc. In some embodiments, the sleeve 180 may be made from Nitinol. The sleeve 180 may have a plurality of slots and/or openings to increase a flexibility of the sleeve 180. By means of non-limiting examples, the sleeve 180 may be implemented using slotted hypotube, coiled sleeve, tungsten-loaded polymer sleeve, or a combination of the foregoing.

In one specific implementation, the proximal segment 300 is made from Molybdenum Rhenium alloy, and the distal segment 120 is made from Nitinol. In another specific implementation, proximal segment 300 is made from Molybdenum Rhenium alloy, and the distal segment 120 is made from stainless steel, or Cobalt-Chromium alloy (e.g., MP35N alloy). In either implementation, the distal segment 120 provides kink resistance and a soft distal end for the guidewire 100, while the proximal segment 300 provides a desired pushability and a desired torqueability. The distal segment 120 may be shapeable during use, and provides desirable shape retention capability (e.g., with or without the aid of the malleable structure 230). Also, because of its relatively high shear modulus, the Molybdenum Rhenium alloy proximal segment 300 provides a desirable torqueability. Furthermore, because of the axial stiffness of the Molybdenum Rhenium alloy segment 300, the guidewire 100 also has a desirable pushability.

Figure 3B:
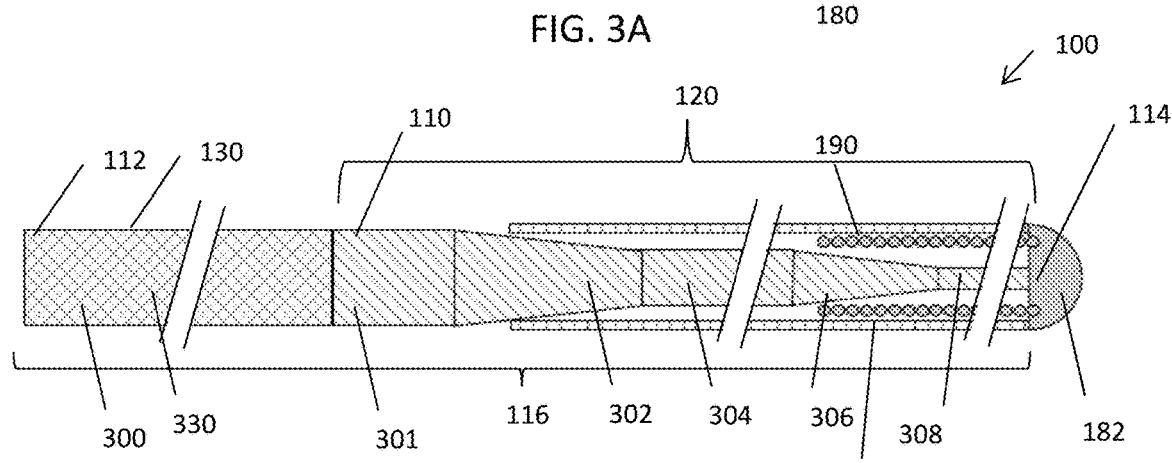
FIG. 3B illustrates the guidewire of FIG. 3A, further having a coil.

Referring to FIG. 3B, in some embodiments, the guidewire 100 may also include a marker coil 190 disposed inside the sleeve 180. As shown in the figure, one end of the marker coil 190 is secured to the tip 182. In other embodiments, the proximal end of the marker coil 190 may be secured to distal segment 120 (e.g., to any location that is proximal to the part 308, such as to the part 306, the part 304, or the part 302, etc.). In other embodiments, the coil 190 may also be coupled to the wall of the sleeve 180. In further embodiments, at least a part of the sleeve 180 may be formed by the marker coil 190. In such cases, the marker coil 190 has a cross sectional dimension that corresponds with (e.g., is the same as) a cross sectional dimension of the sleeve 180. In some cases, an entirety of the length of the sleeve 180 may be made from a coil, such as a marker coil.

Figure 3C:
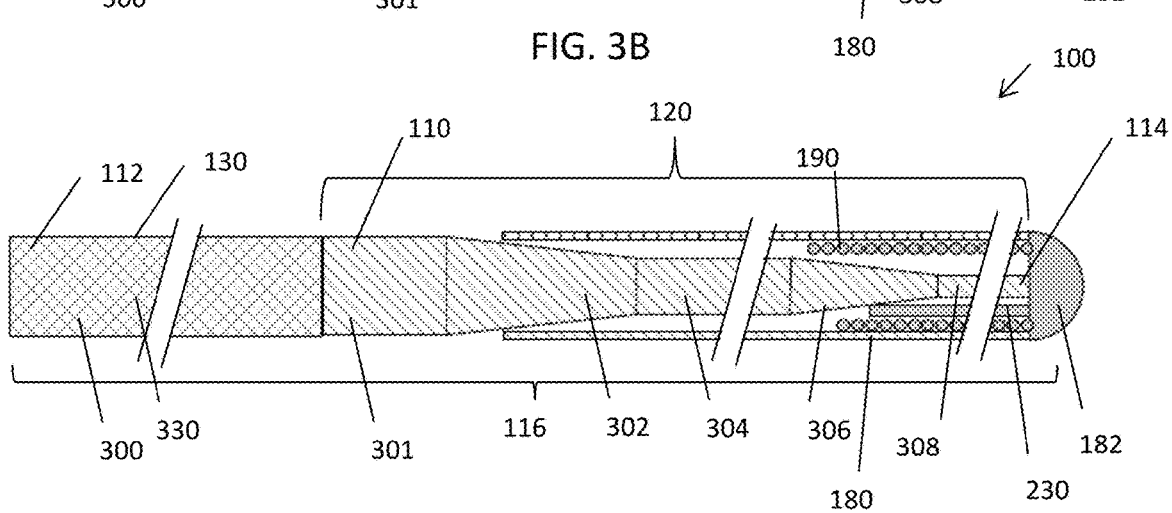
FIG. 3C illustrates the guidewire of FIG. 3B, further having a malleable structure and coil.

In the illustrated embodiments of FIGS. 3A-3B, the distal part 308 of the segment 120 is malleable. Thus, the distal part 308 of the segment 120 is bendable to form a bent shape. The distal part 308 is made from a material that allows it to retain the bent shape after the distal part 308 of the segment 120 is bent. In other embodiments, the distal part 150 may be made from a material that does not have sufficient shape retention capability. In such cases, the guidewire 100 may further include a malleable structure 230 attached to the blunt tip 182 (FIG. 3C). The malleable structure 230 may be inside the sleeve 180. During use, the malleable structure 230 is bendable to form a bent shape and is configured to retain the bent shape after the malleable structure 230 is bent. In some embodiments, the malleable structure 230 may be made from Molybdenum Rhenium alloy or Tungsten Rhenium alloy, in order to provide a desirable shape retention ability for the guidewire 100.

Figure 3D:
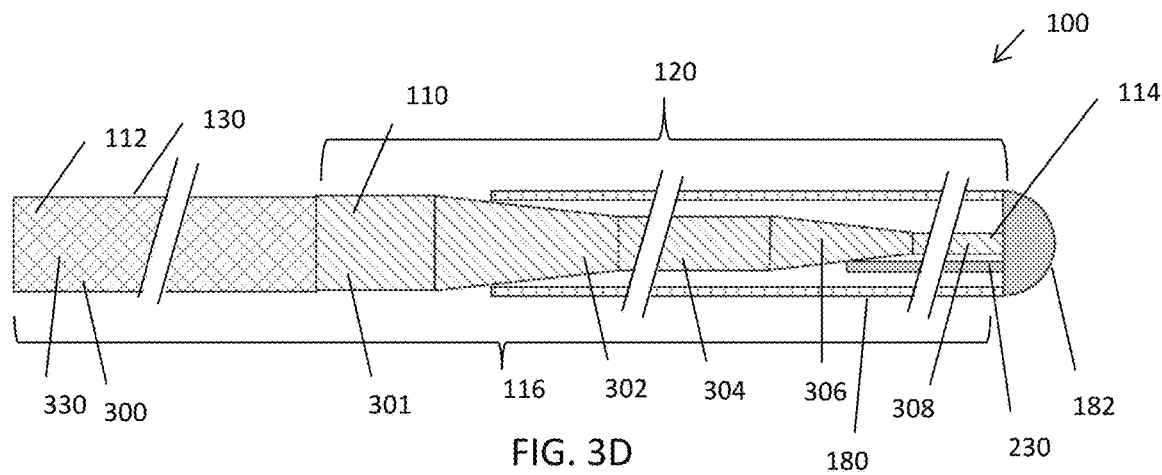
FIG. 3D illustrates the guidewire of FIG. 3A, further having a malleable structure.

In further embodiments, the guidewire may include the malleable structure 230 without the marker coil 190 (FIG. 3D).

It should be noted that the guidewire 100 is not limited to the examples of FIGS. 3A-3D, and that the guidewire 100 may have other configurations in other embodiments. In other embodiments, the guidewire 100 may include more than two segments. For example, in other embodiments, the guidewire 100 may include three or more segments that are connected in series along a longitudinal axis of the guidewire 100. Also, in other embodiments, at least one of the segments may have multiple layers instead of a single layer.

Figure 4:
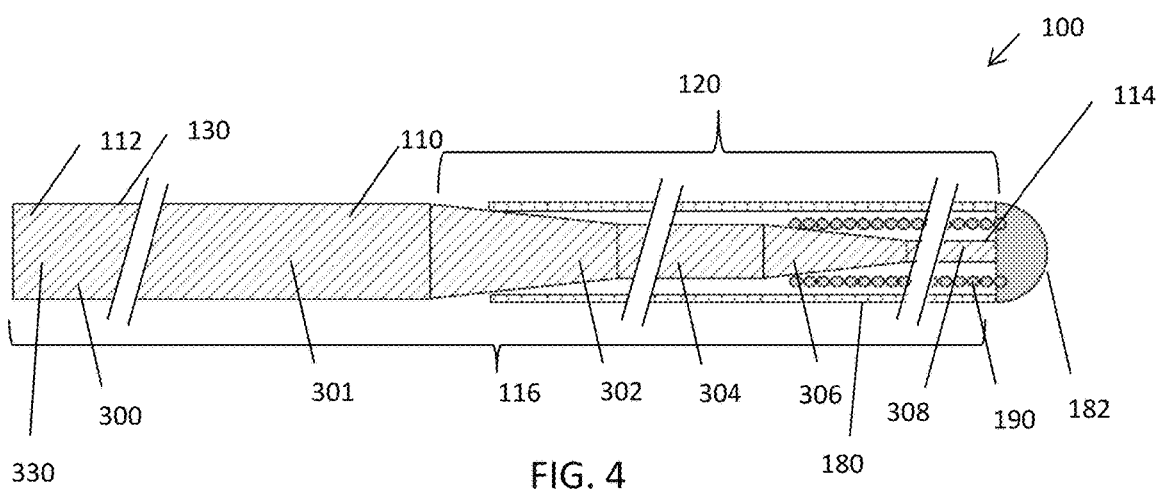
FIG. 4 illustrates a guidewire.

In further embodiments, the proximal segment 300 and the distal segment 120 of the guidewire 100 may be made from a same piece of raw material. FIG. 4 illustrates a guidewire 100 in accordance with some embodiments. The guidewire 100 includes a shaft 110 having a proximal end 112, a distal end 114, and a body 116 extending from the proximal end 112 to the distal end 114. The body 116 of the shaft 110 comprises a distal segment 120 having a plurality of different cross sections along a length of the distal segment 120. At least an outer part 130 of the body 106 that is proximal to the distal segment 120 is made of a material having a shear modulus of at least 13000 ksi. By means of non-limiting examples, the material of the outer part 130 of the body is Molybdenum Rhenium alloy or Tungsten Rhenium alloy.

In the illustrated embodiments, the shaft 110 also includes a proximal segment 300, wherein the proximal segment 300 and the distal segment 120 are made from the same material. In some embodiments, the material of the proximal segment 300 and the distal segment 120 may be Molybdenum Rhenium alloy or Tungsten Rhenium alloy. As shown by the shaded cross section, as a result of using the same piece of raw material to make the segments 300, 120 of the shaft 110, an inner part 330 and the outer part 130 of the segment 300, and the segment 120, have an unity configuration.

As shown in the figure, the proximal segment 300 and the distal segment 120 comprise a single layer, and includes a first part 301, a second part 302, a third part 304, a fourth part 306, and a fifth part 308. The fifth part 308 has a cross sectional dimension that is smaller compared to a cross sectional dimension of the third part 304, and the smaller cross sectional dimension of the fifth part 308 transitions into the larger cross section dimension of the third part 304 via the fourth (intermediate) part 306. Similarly, the fifth third 304 has a cross sectional dimension that is smaller compared to a cross sectional dimension of the first part 301, and the smaller cross sectional dimension of the third part 304 transitions into the larger cross section dimension of the first part 301 via the second (intermediate) part 302. Such configuration is advantageous because it provides progressively softer sections in the proximal-to-distal direction. As a result, the distal segment 120 is softer compared to the remaining part of the body 116, with the distal part 308 providing the softest section, and may flex or bend more easily. In other embodiments, the distal segment 120 may comprise more parts or fewer parts than those described above.

In some embodiments, the part 308 may be compressed to form an elongated cross sectional shape for the part 308. For example, in one implementation, the part 308 may have a circular cross sectional shape, and the part 308 may be compressed into a planar structure having an elongated cross sectional shape, or any of other non-circular cross sectional shape. This feature is advantageous because it provides a bias in the direction of bending for the part 308. The compressing of the part 308 may be achieved by stamping the part 308 in some embodiments.

In the illustrated embodiments, the guidewire 100 also includes a sleeve 180 disposed around the distal end 114 of the shaft 110. As shown in the figure, the sleeve 180 has a blunt tip 182. The distal end 114 of the shaft 110 is coupled to the blunt tip 182. The sleeve 180 may be any tubular member, and may be made from any materials, such as metal, polymer, etc. In some embodiments, the sleeve 180 may be made from Nitinol. The sleeve 180 may have a plurality of slots and/or openings to increase a flexibility of the sleeve 180. By means of non-limiting examples, the sleeve 180 may be implemented using slotted hypotube, coiled sleeve, tungsten-loaded polymer sleeve, or a combination of the foregoing.

As shown in the figure, the guidewire 100 also includes a marker coil 190 disposed inside the sleeve 180. The marker coil 190 is coupled to the tip 182. In some embodiments, the marker coil 190 may also be coupled to the wall of the sleeve 180. In other embodiments, the proximal end of the marker coil 190 may be secured to distal segment 120 (e.g., to any location that is proximal to the part 308, such as to the part 306, the part 304, or the part 302, etc.). The securing may be accomplished using an adhesive, welding, mechanical connector, fusion, etc. In other embodiments, the marker coil 190 may form at least a part of the sleeve 180, or may form an entirety of the sleeve 180. In further embodiments, the guidewire 100 may not include the marker coil 190.

The guidewire 100 of FIG. 4 is advantageous because it provides an optimal combination of shapeability, shape retention capability, and torqueability. Due to the entirety of the shaft 110 of the guidewire 100 being made from the same material (e.g., a single raw member), and the resulting shaft 110 may have a small profile (e.g., smaller than that in the embodiments of FIGS. 1-3). Accordingly, the guidewire 100 may be used to access smaller blood vessels, such as distal blood vessels in a brain, thereby reaching more aneurysms that cannot be accessed before. The distal part 308 provides kink resistance and a soft distal end for the guidewire 100. The distal part 308 and/or the part 304 may be shapeable during use, and provides desirable shape retention capability (without the aid of a malleable structure). However, in other embodiments, the guidewire 100 may optionally further include a malleable structure to enhance the shape retention capability, as similarly discussed. Also, because of its relatively high shear modulus, the shaft 110 made from Molybdenum Rhenium alloy or Tungsten Rhenium alloy provides a desirable torqueability. Furthermore, because of the axial stiffness of shaft 110 made from Molybdenum Rhenium alloy or Tungsten Rhenium alloy, the guidewire 100 also has a desirable pushability.

It should be noted that the materials for making the shaft 110 of the guidewire 100 should not be limited to the examples described, and that the shaft 110 may be made from other materials in other embodiments. For example, in other embodiments, the shaft 110 of the guidewire 100 may be made from other materials, as long as a desired torqueability is achieved. In other embodiments, the shaft 110 may be made from any material having a Young's Modulus (under annealed condition) of at least 6000 ksi, or more preferably at least 30000 ksi, or even more preferably at least 40000 ksi. Also, in other embodiments, the shaft 110 may be made from any material having an ultimate tensile strength (under annealed condition) of at least 100 ksi, and more preferably at least 200 ksi, and even more preferably at least 300 ksi. By means of non-limiting examples, specific materials that may be used include, but are not limited to, Mo-47.5Re, W-25Re, SS304, etc.

In addition, it should be noted that the shaft 110 of the guidewire 100 may have different dimensions in different embodiments. For example, in some embodiments, the shaft 110 of the guidewire 100 may have a total length that is anywhere from 50 inches to 100 inches, such as a length that is anywhere from 70 inches to 90 inches. Also, in some embodiments, the distal segment 120 may have a length that is 5 inches to 30 inches, such as a length that is anywhere from 10 inches to 25 inches, or a length that is anywhere from 12 inches to 20 inches. Furthermore, in some embodiments, the distal part 150/216/308 may have a length that is anywhere from 0.3 inch to 1 inch, such as a length that is anywhere from 0.5 inch to 0.8 inch. In some embodiments in which the distal part 150/216/308 is stamped, the stamped distal part may have a portion with a constant width, wherein the portion may have a longitudinal length of at least 0.3 inch, such as at least 0.4 inch. In addition, in some embodiments, the distal segment 120 may have a cross sectional dimension (e.g., diameter) that is anywhere from 0.04 mm to 0.5 mm and the distal part 150/216/308 may have a cross sectional dimension (e.g., diameter) that is anywhere from 0.004 mm to 0 0.1 mm. In other embodiments, the distal segment 120 and/or the distal part 150/216/308 may have dimensions that are different from those mentioned above.

Furthermore, the number of different cross sections along the length of the distal segment 120 is not limited to the examples described previously. In other embodiments, the number of different cross sections along the length of the distal segment 120 may be more, or fewer, than the ones described herein.

Figure 5:
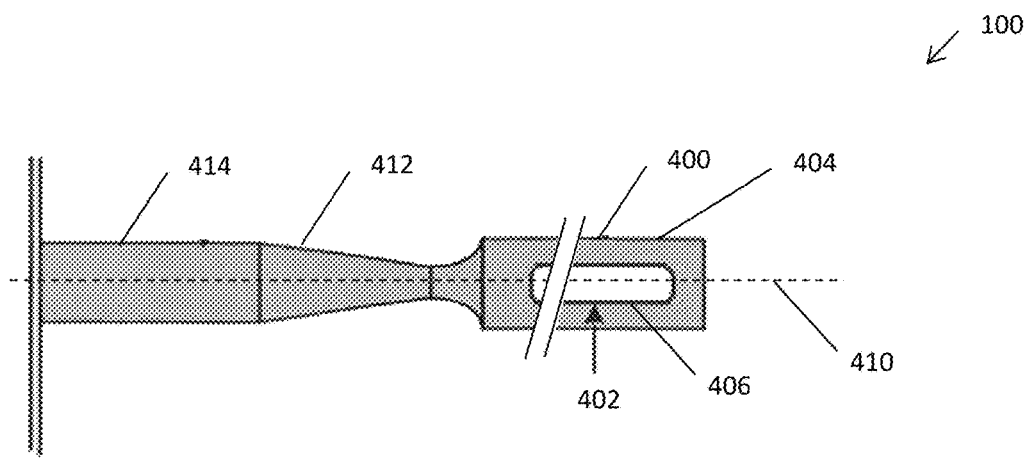
FIG. 5 illustrates another guidewire.

In addition, in one or more embodiments described herein, a part of the segment 120 may have a flat portion. For example, the part 150 (in the embodiments of FIG. 1), the part 216 (in the embodiments of FIG. 2), or the part 308 (in the embodiments of FIG. 3 or 4), may be stamped to create a flat portion. Also, in some embodiments, the flat portion of the segment 120 may include one or more openings extending through a thickness of the flat portion. This feature is advantageous because it may assist the guidewire 100 in achieving a soft distal end without compromising other performance, such as shapeability and/or shape retention of the guidewire 100. FIG. 5 illustrates a guidewire 100 that includes a flat portion 400 with an opening 402. In the illustrated embodiments, the flat portion 400 may be created by stamping a distal end of a shaft, such as the shaft 110 described with reference to any of the embodiments of FIGS. 1-4. As described, the shaft 110 has a proximal end 112, a distal end 114, and a body 116 extending from the proximal end 112 to the distal end 114. The body 116 of the shaft 110 comprises a distal segment 120 having a plurality of different cross sections along a length of the distal segment 120. In other embodiments, the shaft that includes the flat portion 400 may be any elongated member, such as a core wire. The elongated member may have a cross-sectional dimension that is the same along the length of the elongated member, or may have different cross-sectional dimensions along the length of the elongated member.

As shown in FIG. 5, the opening 402 of the flat portion 400 extends through the thickness of the flat portion 400. The flat portion 400 has a long side 404 that is parallel to a longitudinal axis 410 of the flat portion 400. The opening 402 is in a form of an elongated slot, and has a long side 406 that is parallel to the long side 404 of the flat portion 400. The opening 402 of the flat portion 400 is advantageous because it reduces the cross-sectional characteristic (such as moment of inertia) of the flat portion 400. Because a bending stiffness of the flat portion 400 depends on the moment of inertia of the cross-section of the flat portion 400, by reducing the moment of inertia of the cross-section of the flat portion 400, the bending stiffness of the flat portion 400 is also reduced accordingly. Thus, the opening 402 of the flat portion 400 has the benefit of making the flat portion 400 more flexible. The dimension of the opening 402 may be configured to achieve a desired stiffness for the flat portion 400.

In the illustrated embodiments, the guidewire 100 also includes a tapering portion 412 that is proximal the flat portion 400. Also, the guidewire 100 comprises a cylinder portion 414 that is proximal the tapering portion 412. In some embodiments, the cylinder portion 414, the tapering portion 412, and the flat portion 400 may be parts of a shaft (such as, parts of the segment 120 of the shaft 110).

In some embodiments, the flat portion 400 is bendable to form a bent shape and is configured to retain the bent shape after the flat portion 400 is bent. In other embodiments, the flat portion 400 may be made from a material that allows the flat portion 400 to be elastically bendable, so that the flat portion 400 can springs back after being bent.

Figure 6:
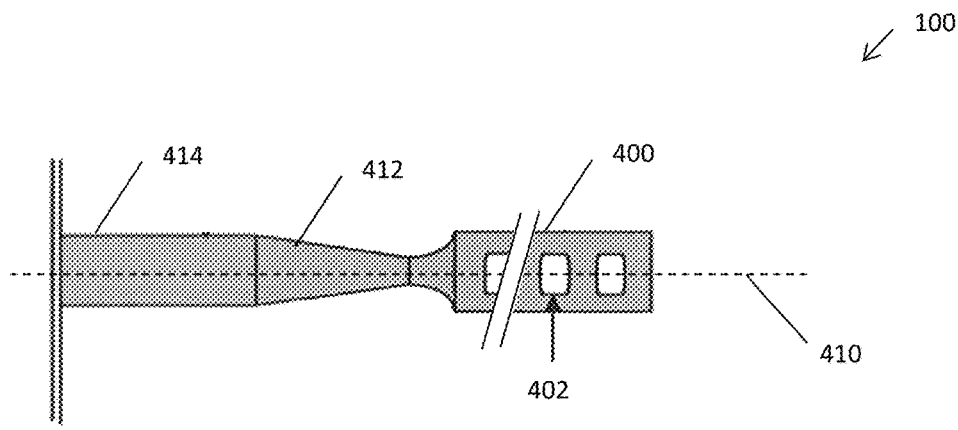
FIG. 6 illustrates another guidewire.
Figures 7, 8:
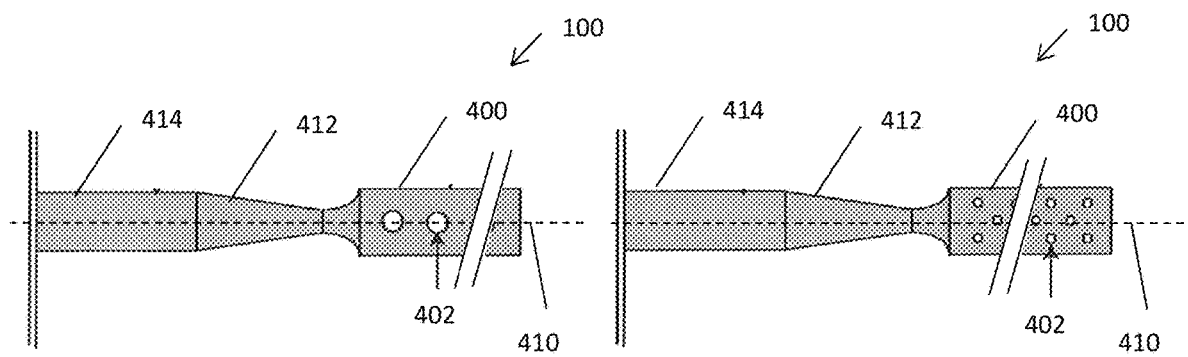
FIG. 7 illustrates another guidewire.
FIG. 8 illustrates another guidewire.

In other embodiments, instead of having a single opening 402, the flat portion 400 may include a series of openings 402 arranged along the longitudinal axis 410 of the flat portion 400 (FIG. 6). As shown in the figure, each of the openings 402 in the series is a rectangular slot extending through the thickness of the flat portion 400. Alternatively, each of the openings 402 in the series may be a circular slot extending through the thickness of the flat portion 400 (FIG. 7). The openings 402 may have other shapes in other embodiments. Furthermore, in other embodiments, the shapes and/or the dimensions of openings 402 of the flat portion 400 may be different. For example, the flat portion 400 may have a first opening 402 with a first shape, and a second opening 402 with a second shape that is different from the first shape.

In the embodiments of FIGS. 6-7, the openings 402 are arranged in a row along the longitudinal axis 410 of the flat portion 400. In other embodiments, as shown in FIG. 8, the openings 402 may be in multiple rows arranged along the longitudinal axis 410, with the openings 402 being in a staggered configuration.

It should be noted that the number of openings 402, the size of the openings 402, the geometry of the openings 402, and the arrangement of the openings 402 are not limited to the examples illustrated. In other embodiments, the number of openings 402, the size of the openings 402, the geometry of the openings 402, the arrangement of the openings 402, or any combination of the foregoing, may be selected or optimized to achieve a desired softness and/or shape retention ability for the distal end of the guidewire 100, depending on the particular application or requirements. Also, in some embodiments, a desired shape retention characteristic of the distal end of the guidewire 100 may be achieved by configuring a thickness of the flat portion 400 of the guidewire 100. For example, the flat portion 400 may be made thicker in some embodiments to enhance the shape retention ability of the distal end of the guidewire 100.

Figure 9:
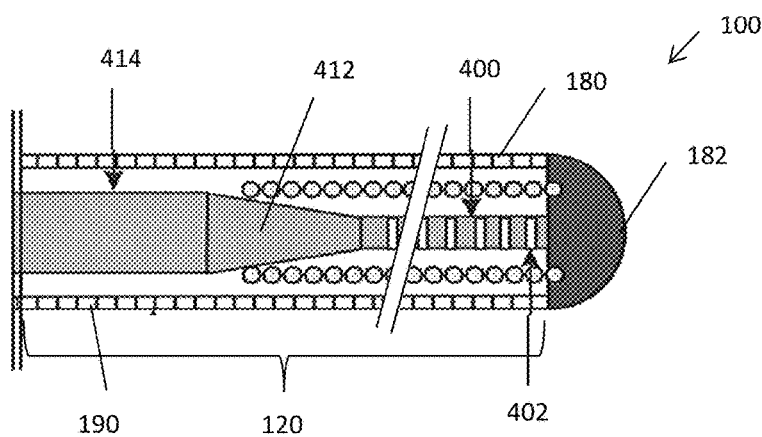
FIG. 9 illustrates another guidewire.

In any of the embodiments of FIGS. 5-8, the guidewire 100 may include other components, such as those similarly described with references to FIGS. 1-4. For example, as shown in FIG. 9, in other embodiments, the guidewire 100 in any of the embodiments of FIGS. 5-8 may also include a sleeve 180 disposed around at least a part of the segment 120. A side view of the flat portion 400 with openings 402 extending through the thickness of the flat portion 400 is also shown. The sleeve 180 may be made from any materials, including but not limited to Nitinol. In some embodiments, the sleeve 180 may include one or more slots extending partially or completely through a thickness of a wall of the sleeve 180. In one implementation, the sleeve 180 may be a slotted Nitinol sleeve. The guidewire 100 may also include a blunt tip 182 to which the segment 120 and/or the sleeve 180 is attached. The guidewire 100 may further include a coil 190 disposed around the segment 120. The coil 190 is located between the segment 120 (e.g., the flat portion 400 of the segment 120) and the sleeve 180. In some embodiments, the coil 190 may be made from a radiopaque material so that that coil 190 can function as a radiopaque coil. In one implementation, the coil 190 may be made from Platinum Tungsten. This is advantageous because the softer radiopaque material of the coil 190 may further increase the softness of the distal tip of the guidewire. In other embodiments, the coil 190 may be made from other materials.

Figure 10A:
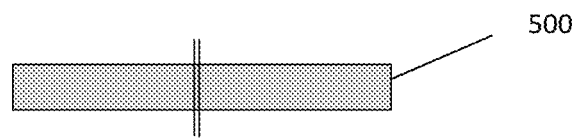
FIGS. 10A-10H illustrates a method of making a guidewire.
Figure 10B:
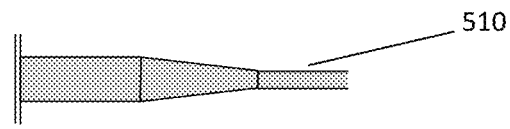
Figure 10C:
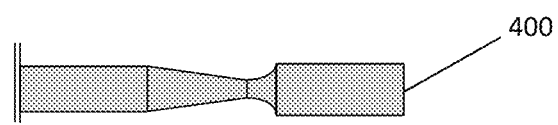
Figure 10D:
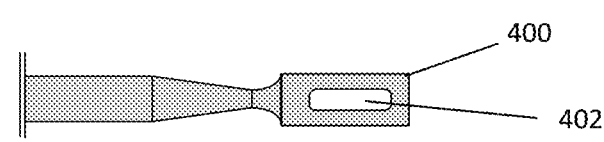
Figure 10E:
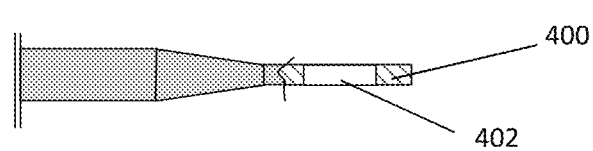
Figure 10F:
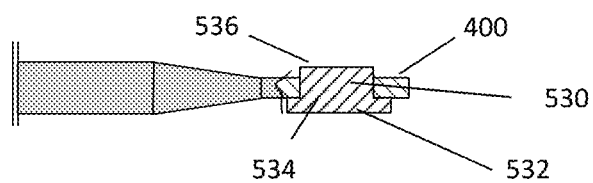
Figure 10G:
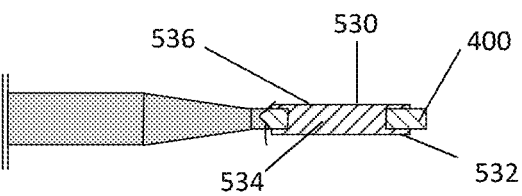
Figure 10H:
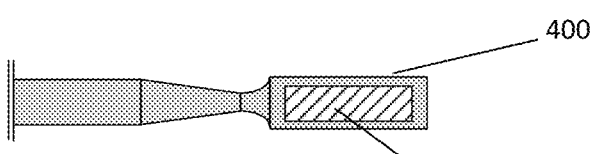

In addition, in one or more embodiments described herein, the guidewire 100 may also include a radiopaque marker coupled to the flat portion 400 of the segment 120. For example, the radiopaque marker may be coupled to the opening 402 at the flat portion 400. FIGS. 10A-10H illustrates a method of making a guidewire that includes a flat portion, and a radiopaque marker coupled to the flat portion. First, a raw wire 500 is provided (FIG. 10A). In some embodiments, the raw wire 500 has a circular cross-section. In other embodiments, the raw wire 500 may have other cross-sectional shapes, such as a square shape, an elliptical shape, a hexagon, an octagon, etc. Next, the raw wire 500 is grounded, cut, and/or sanded to create a shaft 510 having different cross-sectional dimensions along the longitudinal axis of the shaft 510 (FIG. 10B). In other embodiments, the shaft 510 with different cross-sectional dimensions along the longitudinal axis of the shaft 510 may be created using any of the techniques described with reference to FIG. 1F, 2F, or 3A. In further embodiments, the creation of different cross-sectional dimensions along the longitudinal axis of the shaft 510 is optional, and the shaft 510 may have an uniform cross-sectional dimensions along the longitudinal axis of the shaft 510. Next, a portion of the shaft 510 may be stamped to create the flat portion 400 (FIG. 10C). The created flat portion 400 has a first major planar surface, and a second major planar surface that is opposite from the first major planar surface. Then, an opening 402 extending through the thickness of the flat portion 400 may be created. The opening 402 may be created by cutting (e.g., laser cutting, mechanical cutting, etc.) or by puncturing the flat portion 400 in some embodiments (FIG. 10D). FIG. 10E illustrates a side cross-sectional view of the guidewire 100, particularly showing the opening 402 extending through the thickness of the flat portion 400. Next, as shown in FIG. 10F, a radiopaque marker 530 may be inserted into the opening 402 of the flat portion 400. In the illustrated embodiments, the radiopaque marker 530 has a first portion 532 abutting a first side of the flat portion 400, and a second portion 534 configured (e.g., sized and/or shaped) for placement into the opening 402 of the flat portion 400. After the second portion 534 of the radiopaque marker 530 has been placed into the opening 402, a third portion 536 of the radiopaque marker 530 extending from the second portion 534 is located on the opposite side of the flat portion 400. Next, the third portion 536 of the radiopaque marker 530 may be stamped to flatten out the third portion 536. The flattened third portion 536 abuts the second side of the flat portion 400, thereby anchoring the radiopaque marker 530 at the second side of the flat portion (FIG. 10G). As shown in the figure, the first portion 532 of the radiopaque marker 530 has a first cross sectional dimension, the second portion 534 of the radiopaque marker 530 has a second cross sectional dimension, and the third portion 536 of the radiopaque marker 530 has a third cross sectional dimension; wherein the first cross sectional dimension is larger than the second cross sectional dimension; and wherein the third cross sectional dimension is larger than the second cross sectional dimension. FIG. 10H illustrates a top/planar view of the flat portion 400 of the guidewire 100, particularly showing the radiopaque marker 530 being secured to the flat portion 400.

In other embodiments, multiple openings 402 may be created at the flat portion 400 (like those shown in the examples of FIGS. 6-8). In such cases, multiple radiopaque markers 530 may be secured to the flat portion 400 using the technique described with reference to FIGS. 10A-10H.

Figure 11:
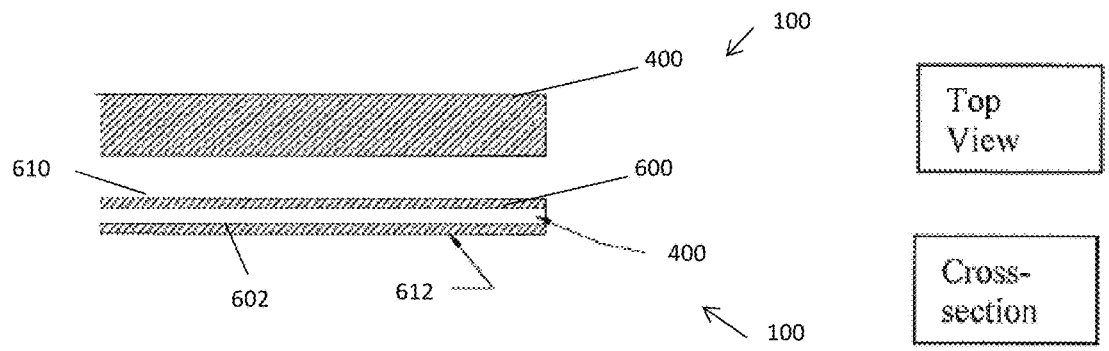
FIG. 11 illustrates a flat portion of a segment of a guidewire.

In other embodiments, instead of anchoring the radiopaque marker 530 against opposite sides of the flat portion 400, other techniques may be utilized to secure the radiopaque marker 530 relative to the flat portion 400. FIG. 11 illustrates another flat portion 400 of a segment of a guidewire 10. The flat portion 400 may be a stamped core wire, as similarly described. As shown in the figure, the flat portion 400 has a first major surface 600 and a second major surface 602 opposite from the first major surface 600. The flat portion 400 comprises a first radiopaque marker 610 secured on the first major surface 600 of the flat portion 400, and a second radiopaque marker 612 secured on the second major surface 602 of the flat portion 400. In other embodiments, the second radiopaque marker 612 is optional, and the guidewire 100 may not include the second radiopaque marker 612.

As shown in FIG. 11, each of the radiopaque marker 610 and the radiopaque marker 612 is a planar marker having a width that is the same as a width of the flat portion 400. In other embodiments, the radiopaque marker 610 and/or the radiopaque marker 612 may have a width that is less than the width of the flat portion 400. In further embodiments, the radiopaque marker 610 and/or the radiopaque marker 612 may have a width that is longer than the width of the flat portion 400.

Various techniques may be employed to secure the marker 610 and/or the marker 612 onto the flat portion 400. For example, the marker 610 and/or the marker 612 may be plated onto the flat portion 400 in some embodiments. In other embodiments, the marker 610 and/or the marker 612 may be secured onto the flat portion 400 via adhesive. In further embodiments, the marker 610 and/or the marker 612 may be applied onto the flat portion 400 through material-deposition techniques. For example, the marker 610 and/or the marker 612 may be achieved by depositing (e.g., electroplating) radiopaque material onto the surface of the flat portion 400. The radiopaque material may be Au, Pt, or other materials. In other embodiments, the flat portion 400 may be dipped into a solution of radiopaque material, which then hardens to form a radiopaque marker circumferentially disposed around the flat portion 400. In such cases, the marker 610 and the marker 612 on opposite sides of the flat portion 400 are parts of the circumferential radiopaque marker surrounding the flat portion 400. The marker 610 and/or the marker 612 is advantageous because, besides being radiopaque for imaging purpose, they also provide shape retention property for the flat portion 400. Accordingly, this feature may eliminate the need to provide a separate bendable structure (that has shape retention characteristic) between the shaft of the guidewire and an outer sleeve of the guidewire.

Figure 12:
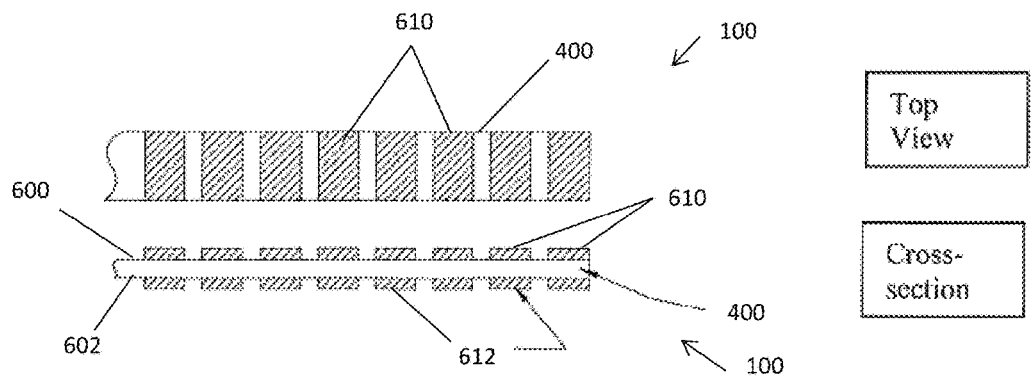
FIG. 12 illustrates another flat portion of a segment of a guidewire.

In other embodiments, instead of having only one radiopaque marker on one side of the flat portion 400 of the guidewire 100, the flat portion 400 may have first multiple radiopaque markers 610 secured on the first major surface 600 of the flat portion 400 (FIG. 12). The first multiple radiopaque markers 610 are arranged in a row along a longitudinal axis of the flat portion 400. Each of the radiopaque markers 610 are spaced apart from each other. As shown in the figure, the guidewire 100 also includes second multiple radiopaque markers 612 secured on the second major surface 602 of the flat portion 400. The second multiple radiopaque markers 612 are arranged in a row along a longitudinal axis of the flat portion 400. Each of the radiopaque markers 612 are spaced apart from each other. In other embodiments, the second multiple radiopaque markers 612 on the second major surface 602 of the flat portion 400 is optional, and the guidewire 100 may not include the second multiple radiopaque markers 612. Various techniques may be employed to secure the markers 610 and/or the markers 612 onto the flat portion 400. For example, the markers 610 and/or the markers 612 may be plated onto the flat portion 400 in some embodiments. In other embodiments, the markers 610 and/or the markers 612 may be secured onto the flat portion 400 via adhesive. In further embodiments, the markers 610 and/or the markers 612 may be applied onto the flat portion 400 through material-deposition techniques. For example, the markers 610 and/or the markers 612 may be achieved by selectively depositing radiopaque material by photolithography or other process onto the surfaces of the flat portion 400. As shown in FIG. 12, the markers 610 and the markers 612 are in the form of radiopaque strips. The markers 610 and/or the markers 612 are advantageous because, besides being radiopaque for imaging purpose, they also serve as stress concentrators and may help in shape retention for the flat portion 400. In other embodiments, the markers 610 and/or the markers 612 may not be in the form of strips, and other patterns of the markers 610/612 may be used.

Figures 13, 14:
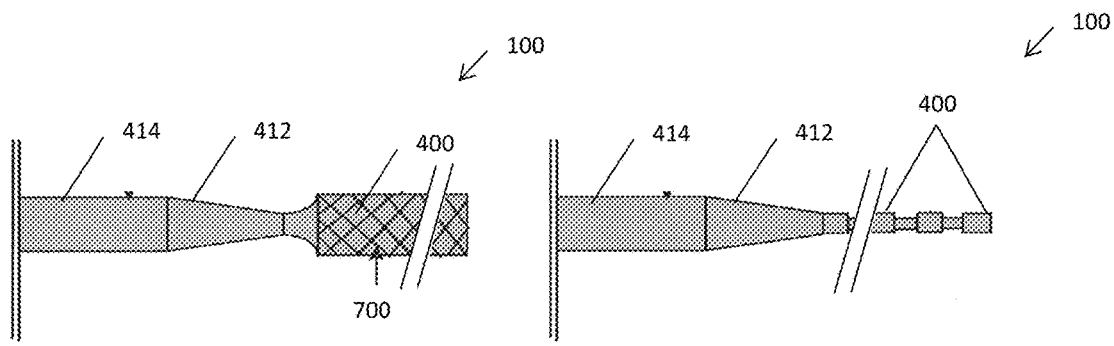
FIG. 13 illustrates another guidewire.
FIG. 14 illustrates another guidewire.

In the above embodiments, the flat portion 400 is described as having one or more openings for reducing a stiffness of the flat portion 400. In other embodiments, other techniques may be employed to reduce a stiffness of the flat portion 400. For example, in other embodiments, the flat portion 400 may include one or more grooves 700 at an exterior surface of the flat portion 400 (FIG. 13). The grooves 700 may be implemented as patterned grooves in some embodiments. The groove(s) 700 reduces the cross-sectional dimension of the flat portion 400, thereby reducing a stiffness (e.g., bending stiffness) of the flat portion 400. In other embodiments, the flat portion 400 may include both groove(s) 700 and opening(s), like the opening(s) 402 described with reference to FIGS. 5-10, to achieve a desired stiffness for the flat portion 400. In further embodiments, the guidewire 100 of FIG. 13 may also include one or more markers secured to the flat portion 400.

In addition, in one or more embodiments described herein, instead of having just one flat portion 400, the segment 120 of the guidewire 100 may include multiple flat portions 400 (FIG. 14). In some embodiments, the flat portions 400 may be created by stamping multiple parts of a core wire that are spaced apart from each other. As a result, each flat portion 400 may have a flat or planar configuration, and adjacent flat portions 400 are connected to each other via a cylindrical portion of the core wire. In other words, a part of the core wire between adjacent flat portions 400 functions as a connecting portion that connects the adjacent flat portions 400. Since the connecting portion and the adjacent flat portions are all made from the same core wire, they have an unity configuration. The flat portions 400 may have the same thickness in some embodiments. In other embodiments, the flat portions 400 may have different respective thicknesses. The number of flat portions 400, the thicknesses of the flat portions 400, the spacing between the flat portions 400, or any combination of the foregoing, may be selected or optimized to achieve a desired softness and/or shape retention ability for the distal end of the guidewire 100. In some embodiments, the guidewire 100 of FIG. 14 may also include one or more markers secured to one or each of the flat portions 400.

Figure 15:
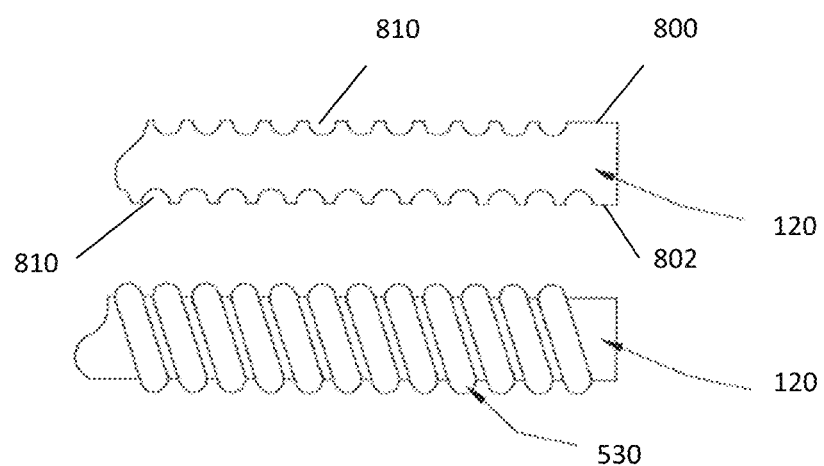
FIG. 15 illustrates a technique for securing a radiopaque marker to a part of a guidewire.

Furthermore, it should be noted that the marker 530 described is not limited to having a planar configuration, and that the manner in which the marker 530 is secured to the shaft is not limited to the examples described. In other embodiments, the marker 530 may have different shapes, and/or the marker 530 may be secured to the shaft in other manners. For example, as shown in FIG. 15, in some embodiments, the marker 530 of the guidewire 100 may be a radiopaque coil 530 surrounding at least a part of a segment 120 of a shaft of the guidewire 100. The part of the segment 120 has opposite sides 800, 802 with indentations 810 along each of the opposite sides for allowing the radiopaque coil 530 to be screwed over the part of the segment 120. In some embodiments, the part of the segment 120 surrounded by the radiopaque coil 530 may be a flat portion (e.g., the flat portion 400 described herein). In such cases, the indentations 810 may be grooves extending through the thickness of the flat portion 400. The indentations 810 may be implemented as cutouts in some embodiments. In other embodiments, the part of the segment 120 surrounded by the radiopaque coil 530 may be another part of the segment 120 that is proximal to the flat portion 400. In further embodiments, the segment 120 surrounded by the radiopaque coil 530 may not be any flat portion. Instead, the segment 120 surrounded by the radiopaque coil 530 may be an un-flattened portion of a core wire or shaft. The technique shown in FIG. 15 for attaching the radiopaque coil 530 to the segment 120 is advantageous because it provides mechanical interaction between the segment 120 and the radiopaque coil 530, and it also save space inside an outer distal sleeve of the guidewire 100.

In any of the embodiments of FIGS. 10-15, the guidewire 100 may include other components, such as those similarly discussed with references to FIGS. 1-4. For example, as similarly discussed with reference to FIG. 9, in other embodiments, the guidewire 100 in any of the embodiments of FIGS. 10-15 may also include a sleeve 180 disposed around at least a part of the segment 120. The sleeve 180 may be made from any materials, including but not limited to Nitinol. In some embodiments, the sleeve 180 may include one or more slots extending partially or completely through a thickness of a wall of the sleeve 180. In one implementation, the sleeve 180 may be a slotted Nitinol sleeve. The guidewire 100 may also include a blunt tip 182 to which the segment 120 and/or the sleeve 180 is attached. The guidewire 100 may further include a coil 190 disposed around at least a part of the segment 120. The coil 190 is located between the segment 120 (e.g., the flat portion 400 of the segment 120) and the sleeve 180. In some embodiments, the coil 190 may be made from a radiopaque material so that that coil 190 can function as a radiopaque coil. In one implementation, the coil 190 may be made from Platinum Tungsten. This is advantageous because the softer radiopaque material of the coil 190 may further increase the softness of the distal tip of the guidewire. In other embodiments, the coil 190 may be made from other materials.

Also, in any of the embodiments described herein, the guidewire 100 may be provided as a part of a medical device. For example, a medical device may include a catheter, and the guidewire 100, wherein the catheter includes a lumen for accommodating the guidewire 100. By means of non-limiting examples, the medical device may be a microcatheter, a balloon catheter, a stent delivery catheter, a catheter for removing blockage in a vessel, a delivery catheter for the guidewire 100, etc.

In one method of use of the guidewire 100, a doctor first bends the distal segment of the guidewire 100 into a desired shape, depending on the geometry of the anatomy that the guidewire 100 will access. For example, the distal segment of the guidewire 100 may be bent to have a L shape, a C shape, a U shape, a S shape, a shape with two or more curves in different planes, etc. The guidewire 100 is then placed in a delivery catheter. Then, an incision is made at a skin of a patient. The delivery catheter with the guidewire 100 therein is inserted through the incision, and into a blood vessel in the patient. The delivery catheter and the guidewire 100 may be advanced distally until the distal end of the guidewire 100 and/or the delivery catheter reaches a target site. The target site may be anywhere in the patient's body, such as a blood vessel in a limb, in a torso, in a neck, in a head, etc. The delivery catheter houses the guidewire 100 as the delivery catheter is advanced distally. When the delivery catheter reaches a location in the patient that requires the bent shape of the distal segment of the guidewire 100 to access, at least a part of the distal segment may be deployed out of the delivery catheter to let the distal segment assumes its bent shape. The bent shape of the distal segment of the guidewire 100 steers the guidewire 100 into a desired direction, thereby allowing the guidewire 100 and the delivery catheter to be advanced distally into a desired passage. The guidewire 100 described herein is advantageous because it allows a bent shape of the distal segment of the guidewire 100 to be retained, so that the bent shape will not return back to the pre-bent configuration even after the distal segment has traversed different paths in a vessel with different curvatures (or even after the bent distal segment has been placed in a tube, such as a delivery tube). The guidewire 100 is also advantageous because it allows the doctor to effectively torque the guidewire 100 due to the enhanced torqueability of the guidewire 100, and allows the doctor to push the guidewire 100 distally inside the patient without kinking.

Embodiments of the guidewire 100 described herein have desired torqueability, desired shape retention capability, desired pushability, or any combination of the foregoing. In some embodiments, a desired torqueability is considered to be achieved by the guidewire 100 if a twisting or torqueing motion applied at a proximal end about a longitudinal axis of the guidewire 100 to turn the proximal end of the guidewire 100 (or shaft 110) by an angle P will result in a turning of the distal end of the guidewire 100 by an angle D that is at least 80% of P, or more preferably at least 90% of P, or even more preferably at least 95% of P (e.g., 100% of P, which means that the distal end of the guidewire 100 has 1:1 response with respect to a torque applied at the proximal end of the guidewire 100). Also, in some embodiments, a desired shape retention capability is considered to be achieved by the guidewire 100 if the bent segment with curvature can retain at least 70% of the curvature, or more preferably at least 80% of the curvature, and even more preferably at least 90% of the curvature, after the bent segment is placed in a tube and is pushed back out from the tube. Also, in some embodiments, a desired pushability may be achieved if the guidewire 100 does not kink while being advanced inside a vessel.

The following items are exemplary features of embodiments described herein. Each item may be an embodiment itself or may be a part of an embodiment. One or more items described below may be combined with other item(s) in an embodiment.

Item 1: A guidewire includes: a shaft having a proximal end, a distal end, and a body extending from the proximal end to the distal end; a blunt tip; and a sleeve; wherein the body of the shaft comprises at least a segment that is surrounded by the sleeve, the segment coupled to the blunt tip; and wherein the segment of the body of the shaft comprises a flat portion having one or more openings extending through a thickness of the flat portion.

Item 2: The one or more openings comprise only one elongated slot extending through the thickness of the flat portion.

Item 3: The flat portion has a long side that is parallel to a longitudinal axis of the guidewire, and wherein the slot has a long side that is parallel to the long side of the flat portion.

Item 4: The one or more openings comprise a series of openings arrange along a longitudinal axis of the flat portion.

Item 5: Each of the openings in the series is a rectangular slot extending through the thickness of the flat portion.

Item 6: Each of the openings in the series is a circular slot extending through the thickness of the flat portion.

Item 7: The one or more openings comprise rows of openings arranged in a staggered configuration.

Item 8: The guidewire further includes a radiopaque marker extending through one of the one or more openings.

Item 9: The radiopaque marker has a first portion abutting a first side of the flat portion, a second portion within the one of the one or more openings, and a third portion abutting a second side of the flat portion, the second side being opposite from the first side of the flat portion.

Item 10: The first portion of the radiopaque marker has a first cross sectional dimension, the second portion of the radiopaque marker has a second cross sectional dimension, and the third portion of the radiopaque marker has a third cross sectional dimension; wherein the first cross sectional dimension is larger than the second cross sectional dimension; and wherein the third cross sectional dimension is larger than the second cross sectional dimension.

Item 11: The flat portion comprises a stamped core wire.

Item 12: The guidewire further includes a coil disposed between the flat portion and the sleeve.

Item 13: The coil is made from a radiopaque material.

Item 14: The coil is made from Platinum Tungsten.

Item 15: The sleeve is made from Nitinol.

Item 16: The sleeve comprises a plurality of slots.

Item 17: The body of the shaft comprises a tapering portion that is proximal the flat portion.

Item 18: The body of the shaft comprises a cylinder portion that is proximal the tapering portion.

Item 19: The flat portion is bendable to form a bent shape and is configured to retain the bent shape after the flat portion is bent.

Item 20: The segment also comprises an additional flat portion distal to the flat portion.

Item 21: The segment also comprises a connecting portion connecting the flat portion and the additional flat portion, wherein the connecting portion, the flat portion, and the additional flat portion have an unity configuration.

Item 22: A medical device includes a catheter, and the guidewire, wherein the catheter includes a lumen for accommodating the guidewire.

Item 23: A guidewire includes: a shaft having a proximal end, a distal end, and a body extending from the proximal end to the distal end; a blunt tip; and a sleeve; wherein the body of the shaft comprises at least a segment that is surrounded by the sleeve, the segment coupled to the blunt tip; and wherein the segment of the body of the shaft comprises a flat portion with a first major surface and a second major surface opposite from the first major surface, and wherein the flat portion comprises one or more radiopaque markers secured on the first major surface.

Item 24: The one or more radiopaque markers comprise a first planar marker having a width that is the same as a width of the flat portion.

Item 25: The guidewire further includes a second planar marker secured on the second major surface of the flat portion.

Item 26: The one or more radiopaque markers comprise first multiple radiopaque markers spaced apart from each other.

Item 27: The first multiple radiopaque markers are aligned in a row along a longitudinal axis of the flat portion.

Item 28: The guidewire further includes second multiple radiopaque markers spaced apart from each other and secured on the second major surface of the flat portion.

Item 29: The flat portion also comprises one or more radiopaque markers secured on the second major surface.

Item 30: A guidewire includes: a shaft having a proximal end, a distal end, and a body extending from the proximal end to the distal end; a blunt tip; and a sleeve; wherein the body of the shaft comprises at least a segment that is surrounded by the sleeve, the segment coupled to the blunt tip; and wherein the segment of the body of the shaft comprises a flat portion with an exterior surface, and wherein the flat portion comprises a plurality of grooves at the exterior surface.

Item 31: A guidewire includes: a shaft having a proximal end, a distal end, and a body extending from the proximal end to the distal end; a blunt tip; and a sleeve; wherein the body of the shaft comprises at least a segment that is surrounded by the sleeve, the segment coupled to the blunt tip; and wherein the guidewire further comprises a radiopaque coil surrounding at least a part of the segment, the part of the segment having opposite sides with indentations along each of the opposite sides for allowing the radiopaque coil to be screwed over the part of the segment.

Item 32: The part of the segment comprises a flat portion.

Item 33: The segment comprises a flat portion, and the part of the segment is proximal to the flat portion.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. A guidewire, comprising:
a shaft having a proximal end, a distal end, and a body extending from the proximal end to the distal end;
a blunt tip; and
a sleeve,
wherein the body of the shaft comprises at least a segment that is surrounded by the sleeve, the segment coupled to the blunt tip,
wherein the segment of the body of the shaft comprises a flat portion having a width perpendicular to a longitudinal axis of the shaft, and a thickness that is less than the width, wherein the flat portion has one or more openings extending through the thickness of the flat portion from a first surface of the flat portion to a second surface of the flat portion opposite the first surface, and wherein one of the one or more openings is at a center of the width of the flat portion, and wherein the one or more openings comprise an elongated opening at the first surface, the elongated opening extending through the thickness of the flat portion, wherein the flat portion has a long side that is parallel to a longitudinal axis of the guidewire, and wherein the elongated opening has a long side that is parallel to the long side of the flat portion, and a short side that is perpendicular to the long side of the flat portion.

2. A guidewire, comprising:
a shaft having a proximal end, a distal end, and a body extending from the proximal end to the distal end;
a blunt tip; and
a sleeve;
wherein the body of the shaft comprises at least a segment that is surrounded by the sleeve, the segment coupled to the blunt tip;
wherein the segment of the body of the shaft comprises a flat portion having a width perpendicular to a longitudinal axis of the shaft, and a thickness that is less than the width, and wherein the flat portion has one or more openings extending through the thickness of the flat portion from a first surface of the flat portion to a second surface of the flat portion opposite the first surface;
wherein the guidewire further comprises a radiopaque marker extending through one of the one or more openings, wherein the radiopaque marker has a first portion abutting the first surface of the flat portion, a second portion within the one of the one or more openings, and a third portion abutting the second surface of the flat portion.

3. The guidewire of claim 2, wherein the first portion of the radiopaque marker has a first cross sectional dimension, the second portion of the radiopaque marker has a second cross sectional dimension, and the third portion of the radiopaque marker has a third cross sectional dimension;
wherein the first cross sectional dimension is larger than the second cross sectional dimension; and
wherein the third cross sectional dimension is larger than the second cross sectional dimension.

4. A guidewire, comprising:
a shaft having a proximal end, a distal end, and a body extending from the proximal end to the distal end;
a blunt tip; and
a sleeve;
wherein the body of the shaft comprises at least a segment that is surrounded by the sleeve, the segment coupled to the blunt tip;
wherein the segment of the body of the shaft comprises a flat portion having a width perpendicular to a longitudinal axis of the shaft, and a thickness that is less than the width, and wherein the flat portion has one or more openings extending through the thickness of the flat portion from a first surface of the flat portion to a second surface of the flat portion opposite the first surface; and
wherein the segment further comprises an additional flat portion distal to the flat portion, and a connecting portion connecting the flat portion and the additional flat portion, wherein the connecting portion, the flat portion, and the additional flat portion have a unity configuration.

* * * * *